United States Patent [19]
Abul-Faraj et al.

[11] Patent Number: 5,416,330
[45] Date of Patent: May 16, 1995

[54] RADIATION MONITORING SYSTEM FOR CONTAINERS, LIVESTOCK, AND FOODSTUFF

[75] Inventors: Waleed H. Abul-Faraj; Abdul-Rahman A. F. Abdul-Fattah, both of Jeddah, Saudi Arabia; Herman M. Daniel, Moylan, Pa.; Abdo A. Husseiny, LaPlace, La.

[73] Assignee: Technology International Incorporated, LaPlace, La.

[21] Appl. No.: 978,284

[22] Filed: Nov. 18, 1992

[51] Int. Cl.⁶ ..................... G01T 1/163; G01T 1/167
[52] U.S. Cl. ............................. 250/395; 209/589; 250/394
[58] Field of Search ............... 250/395, 394, 361 R, 250/363.02; 209/589

[56] References Cited

U.S. PATENT DOCUMENTS

| | | | |
|---|---|---|---|
| 3,084,255 | 4/1963 | Brinkerhoff et al. | 250/380 |
| 3,872,306 | 3/1975 | Palmer | 378/51 |
| 4,194,634 | 3/1980 | Kelly | 209/589 |
| 4,263,098 | 4/1981 | Kasperek et al. | 376/159 |
| 4,445,615 | 5/1984 | Böhme et al. | 209/555 |
| 4,539,648 | 9/1985 | Schatzki | 364/555 |
| 4,646,978 | 3/1987 | Johnson et al. | 241/24 |
| 4,654,142 | 3/1987 | Thomsen et al. | 210/232 |
| 5,067,616 | 11/1991 | Plester et al. | 209/3.1 |

FOREIGN PATENT DOCUMENTS

| | | | |
|---|---|---|---|
| 3914864 | 11/1990 | Germany | 250/363.01 |
| 62-17681 | 1/1987 | Japan | 250/394 |

OTHER PUBLICATIONS

Grafton D. Chase and Joseph L. Rabinowitz, *Prinicples of Radioisotope Methodology*. Third Edition. Burgess Publishing Company, Minneapolis (1967) p. 478.

G. S. Smith, T. G. Lohman, B. C. Breidenstein, and A. R. Twardock, "ILLASCO . . . Can it Predict Lean Meat from Radioactivity of the Animal?" Presented at *Symposium on Uses of Atomic Energy in Animal Science*, 56th meeting of the American Society of Animal Science, Knoxville, Tennessee (Aug. 13, 1964), pp. 1–18.

*Primary Examiner*—Constantine Hannaher
*Attorney, Agent, or Firm*—Sixbey, Friedman, Leedom & Ferguson; Gerald J. Ferguson, Jr.; Donald R. Studebaker

[57] ABSTRACT

Radiation monitoring systems for crates and containers, and small volumes of foodstuff and tobacco, and whole body animal monitoring system for measuring the radiation contamination levels of containers, foodstuff, tobacco or animals and in the case of animals particularly, livestock utilized for meat consumption. The containers or animals are weighed, identified and then directed through a specially constructed shielded holding area, wherein multiple radiation detectors measure the radiation level for the containers or animal in the pen. A microprocessor analyzes the data information and provides a respective output for each container or animal which in turn is compared with predetermined standards and input information. The particular reading per container or each animal monitored actuates controls to segregate the containers or animals by those having acceptable and non-acceptable levels of radiation. The non-acceptable segregated containers or animals are specially held for evacuation and for disposal. In case of small volumes of grocery, a small scale radiation monitoring system provides the user indication of fitness of the product for human consumption.

62 Claims, 35 Drawing Sheets

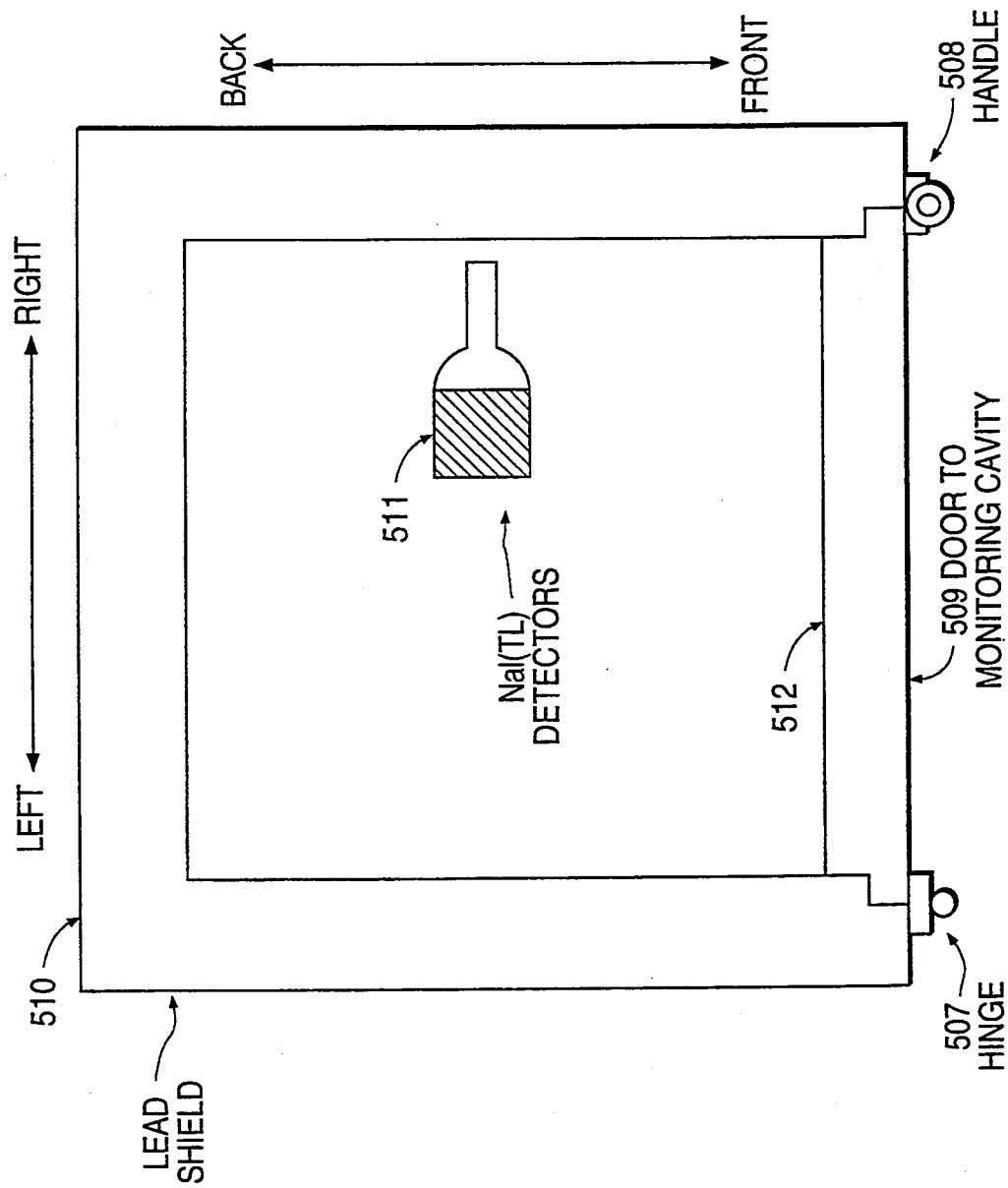

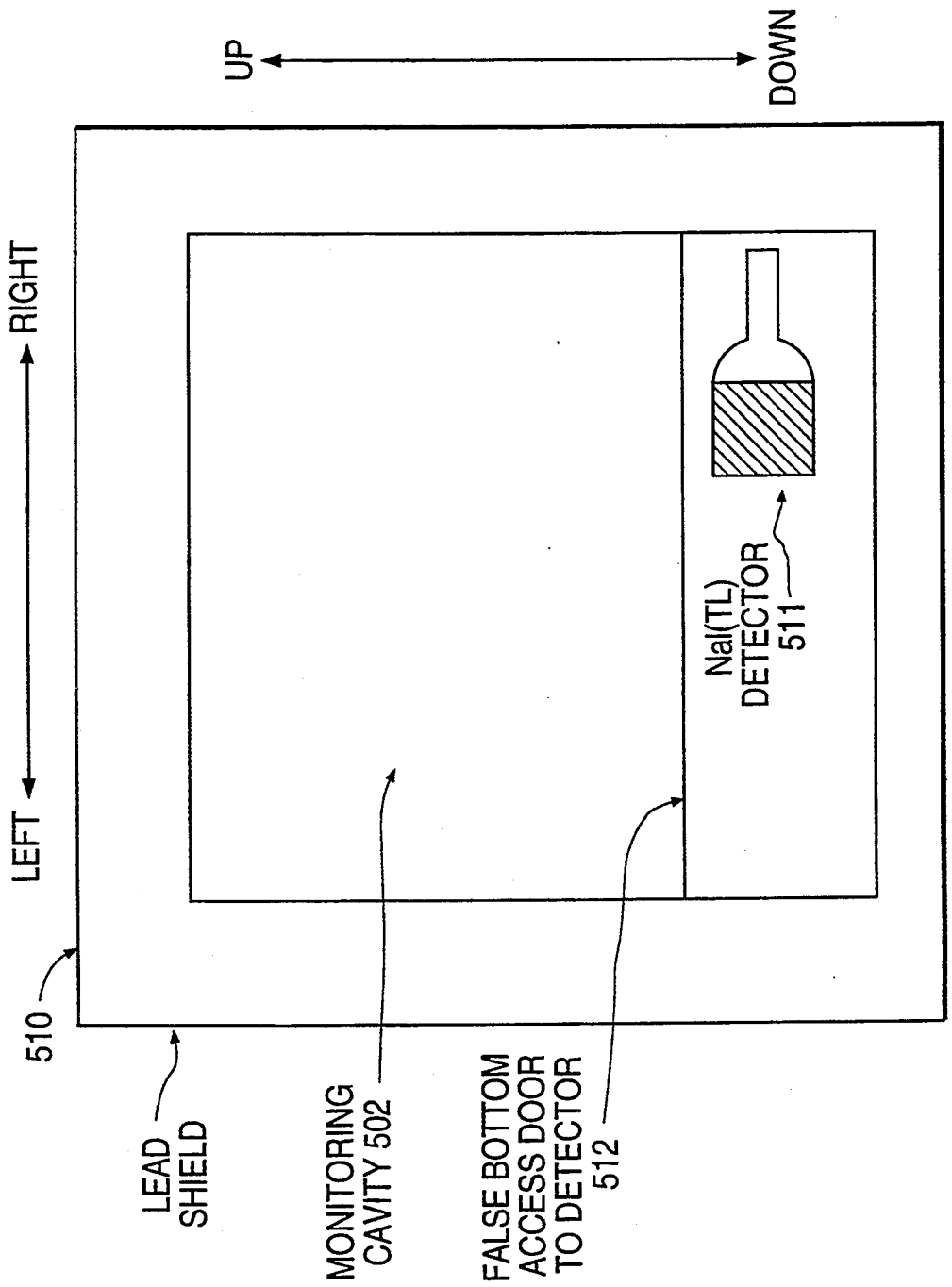

RADIATION MONITORING SYSTEM FOR CONTAINERS, LIVESTOCK, AND FOODSTUFF

BACKGROUND OF THE INVENTION

1. Field of the Invention

The present invention relates to the field of radiation detection of live animals, foodstuff, goods for human consumption, containers, and crates for the purpose of segregating them based upon radioactivity present therein.

2. The Prior Art

Contamination by various forms of radiation is known to affect the environment, including the soil, bodies of water, and the atmosphere. Such contamination has various causes, such as natural radiation, nuclear accidents, and nuclear tests. Additionally, radioactive waste materials may leak into the air, the water, and the soil through various pathways.

Such radioactive contamination affects animals which graze upon plants growing in fields, with radioactivity from such plants being taken up by the animals. Such grazing animals can absorb radiation through various additional pathways, such as by the drinking water used, and by fallout of radioactive particles landing directly upon the animals, for example.

It has been determined that such grazing livestock can absorb levels of radiation which would render the meat from the animal unfit to meet governmental regulations for the limits for safe consumption.

Livestock is shipped all over the world, so that animals in an area affected by radiation contamination, may be introduced into various countries or states which are relatively unaffected by such contamination. Accordingly, various governmental entities exist which may test such livestock for radiation contamination.

Accordingly, there is a need in the art for a system for detecting radiation levels in individual animals, and for segregating the animals based upon their radiation content. There is furthermore a need for a system for determining the radiation concentration in livestock, that is, a system which determines the amount of radiation per pound of a given animal, and for segregating same based upon predetermined limits.

Similarly, produce may be radioactively contaminated. Produce is ordinarily shipped throughout the world, and various governmental bodies may exist in various countries and states, to set safety standards for radiation concentration in produce.

Accordingly, there is a need for a system for screening produce to determine radiation concentration therein, that is, to determine the radiation concentration of the produce per unit weight, and for segregating the produce based upon the levels of radiation concentration therein.

Additionally, crates of various types are used for shipping articles throughout the world. There is therefore a need for radiation screening of such crates, to sort or segregate such crates based upon the radiation concentration therein.

Furthermore, retail goods for human consumption such as foodstuff including produce, milk, milk products, cereals, flour, meats, and meat products; beverages including juices carbonated drinks, coffee, tea, etc.; and tobacco may be radioactively contaminated. Foodstuff and beverages are ordinarily shipped throughout the world frozen, packaged, canned, dried, or fresh, and tobacco is supplied in various forms raw, processed, snuff, chewing, cigars, cigarettes, etc. and various international bodies and local governmental bodies may exist in various countries and states, to set safety standards for radiation concentration in each type of product for human consumption as it pertains to human intake. However, contamination of such retail goods may escape detection at ports of entry and be sold in the local markets of various countries, and tobacco specially, is frequently contaminated with high levels of radioactive material, naturally occurring in soil such as Polonium-210 and Radium-222 and escapes detection prior to entering the market place.

Accordingly, there is a need for a small scale radiation monitoring system for screening foodstuff, produce, beverages and tobacco by individuals at home, restaurants, or local grocery stores to determine, radiation concentration therein, that is, to determine the radiation concentration of the consumption goods per unit weight, and for visual indication of whether or not the goods meet the requirements for human intake or use based upon levels of radiation concentration therein and based on degree of personal aversion to risk.

The prior art includes measuring devices and systems for determining radioactivity in articles, as well as for systems for sorting articles depending on some predetermined characteristic. Examples of such prior art are discussed hereunder.

In U.S. Pat. No. 4,445,615, sorting based on radiation count of a detector is adjusted depending upon the presence of adjacent particles. This reference acknowledges that the radiation count depends upon a variety of unaccounted-for factors including mass of the particles. This reference fails to teach accounting for mass of the particles in computing radiation concentration, nor does this reference teach sorting particles based upon their actual radiation concentration (rather than on the estimated concentration).

In U.S. Pat. No. 4,646,978, a method for sorting radioactive waste is taught. Low revel radioactive waste can be sorted; however, there is no teaching or suggestion of determining actual radiation concentration of individual pieces of waste by weighing thereof, nor does it teach performing a computation of radiation concentration based upon actual weight of individual pieces.

U.S. Pat. No. 3,872,306, disclosed separation of potatoes from stones by use of a control unit, conveying means, and a radiation detector (which, however, detects radiation from a radiation source 22 which generates X-rays), and deflecting devices. However, no weighing step is taught, nor is a concentration-determining step taught based upon actual weight of individual potatoes or stones.

U.S. Pat. No. 4,194,634 teaches an apparatus for sorting radioactive material and includes a control unit. The control unit has a cut-off grade radiation rate, for determining whether to reject the particle. The particles must, however, be closely sized since there is no teaching of weighing of individual particles and then computing a radiation concentration based upon this weight.

U.S. Pat. No. 3,828,193 relates to detecting missing or partially-filled containers in a sealed shipping carton. U.S. Pat. No. 4,263,098 relates to determination of concentration of fats in meat using gamma detectors; however, no means for sorting is disclosed. U.S. Pat. No. 4,539,648 relates to detection of agricultural contraband in baggage, and relates to image-formation techniques.

U.S. Pat. No. 4,658,142 relates to a particular apparatus for detecting radiation in a container; however, no sorting or weighing means are taught to base segregation of containers based upon their radiation concentration.

None of the prior art references disclose a process which includes the steps of detecting radiation counts from the whole body of a live animal, weighing the animal, determining the radiation concentration of the animal, and then segregating the livestock based upon their radiation concentration; a process which includes the steps of detecting radiation from a container, weighing the container, determining the radiation concentration of the container, and then segregating the containers based upon their radiation concentration; or a process for small scale radiation monitoring of human consumption goods which includes the steps of detecting radiation from grocery bags, weighing the grocery, determining the radiation concentration of foodstuff, beverages or tobacco, and indication of the suitability for human use or intake on a radiation level meter.

SUMMARY OF THE INVENTION

According to the present invention, a system is shown for detecting radiation levels in livestock. In another aspect of the invention, a system detects radiation levels in crates and other containers, and segregates same according to the predetermined levels of radiation concentration therein. In a third aspect of the invention, a small-scale system detects radiation levels in grocery bags and similar packages, containing foodstuff, beverages, or tobacco, and indicates whether or not the goods are fit for human intake.

The radiation monitoring system of the present invention, for crates and large containers, detects traces of radiation contamination in closed crates and large containers without need for random sampling of contents. The system includes a high voltage supply and accessories, an analyzer, a tagging system, a scale, a microprocessor, and a conveyer system. The scanning analyzer includes gamma detectors, a shield, a liner, sealed watertights and a multi-channel analyzer with associated electronics and ancilaries. The inventive process encompasses four steps for each container, namely to identify the container, weigh it, measure the radiation level, and to segregate containers based on their radiation concentration. This purpose is useful in determining fitness of consumption of foodstuffs or other use of goods in the container by the public at large.

In a second aspect of the invention, drawn to a whole body radiation counter for livestock, there is included a high voltage supply and accessories, an analyzer, a tagging system, a scale, a microprocessor, and a series of automatically actuated gates, chutes, and holding pens for directing the animals and for rapid processing. The scanning analyzer includes a shield, a liner, watertight seals, a multi-channel analyzer with associated electronics and ancillaries, and gamma radiation detectors. The process according to the invention identifies each animal, weighs the animal, measures the radiation level, and segregates animals based upon the whole body radiation concentrations therein. All of the foregoing discussion with respect to the prior art references, can be applied here with only minor additional distinctions. Such minor additional distinctions are that animals cannot be divided as might a container, and that many prior art tests are not suitable for use with animals, where such tests involve intense radiation bombardment which causes radiation to pass through an animal and to a detector (that is, without causing death or illness of the animal).

In a third aspect of the invention, drawn to radiation monitor for small quantities of foodstuff, or tobacco, which are typically used at home, there is included a lead box with thick walls for radiation shielding, a monitoring cavity to define the area for placing food or tobacco to be monitored, made from a low radiation background durable material such as stainless steel, detectors, high voltage bias supply, single channel analyzer, count rate meter, and amplifier. The process according to the invention, measures the radiation level, and provides the homemaker or the user with indication of whether or not the product is suitable for human intake. The inventive process encompasses two steps for each package or grocery bag, namely to identify the radiation level, and to determine the safety of consumption of the foodstuff, beverages, produce, or tobacco by human.

Accordingly, it is an object of the present invention to provide a radiation monitoring system for determining radiation concentration in livestock, crates, containers, or small quantities of food, beverage or tobacco.

It is another object of the present invention to provide a system for determining radiation concentration in livestock, crates, containers, or small quantities of goods for human consumption, and for segregating same based on the level of radiation concentration detected.

It is a further object of the present invention to provide a system for rapidly screening livestock, crates, or other containers to minimize storage and holding facilities and to avoid economic penalties for the supplier and the receiver from long delays.

It is still a further object of the present invention to enable individuals to screen goods for individual consumption to determine the fitness of same for human intake based on radiation level.

It is still a further object of the present invention to process the livestock, crates, or other containers in confined space and radiation-shielded chambers to prevent the exposure of the system operators.

It is still a further object of the present invention to provide a system for automatically handling livestock, crates, or other containers including automated data handling equipment for identifying individual ones of the livestock, crates, or other containers.

BRIEF DESCRIPTION OF THE DRAWINGS

FIG. 37 is a cutaway view down of the system shown in FIG. 35; and

FIG. 38 is a cutaway front looking back of the system shown in FIG. 35.

DETAILED DESCRIPTION OF THE INVENTION

Figure 1:
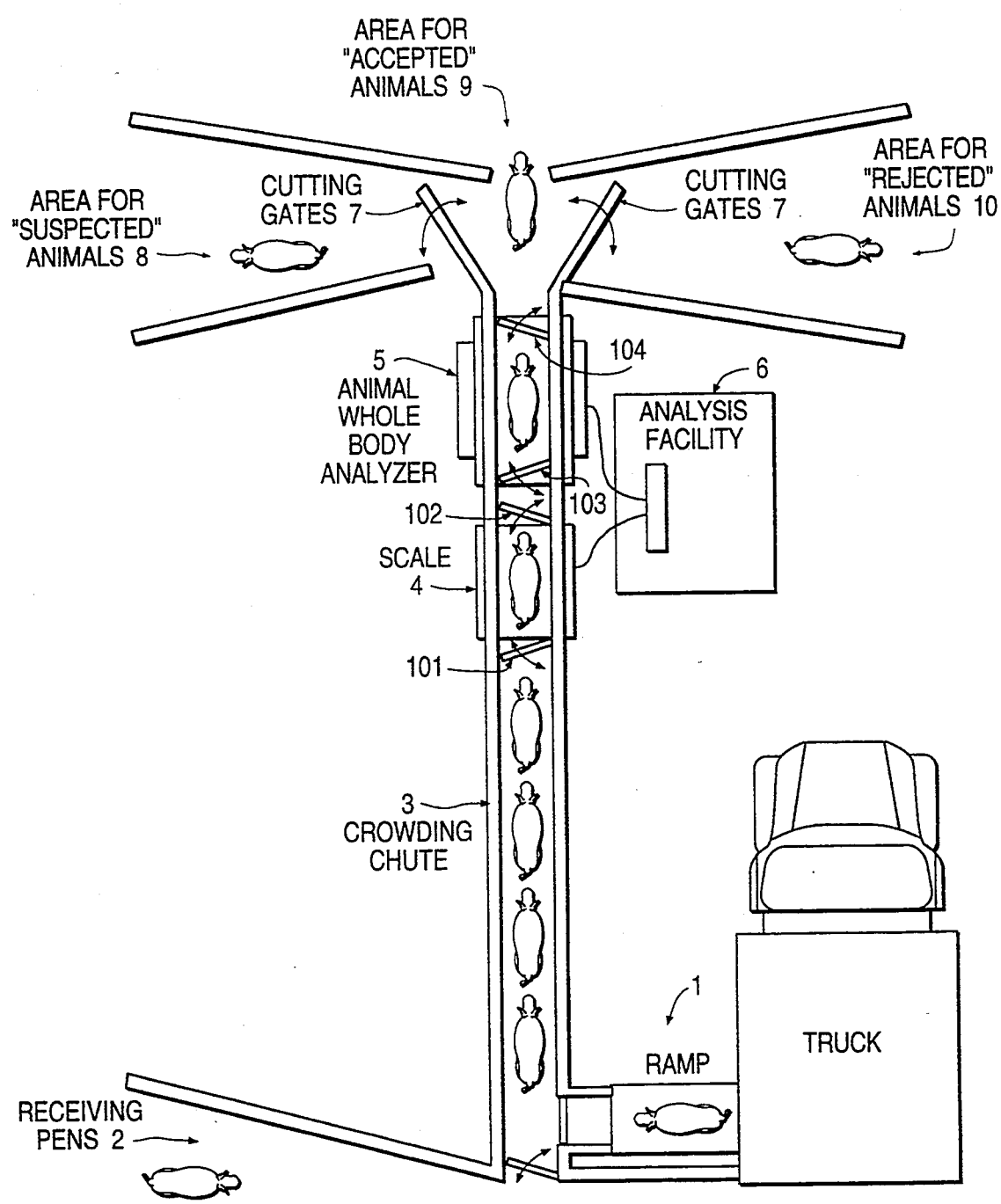
FIG. 1 is a schematic view of a livestock whole body radiation monitoring system.

The schematic diagram shown in FIG. 1 illustrates schematically main process steps and equipment according to the present invention. Livestock animals are provided either from a receiving pen 2 or a truck via a ramp 1, to a crowding chute 3. Animals are separately weighed at a scale 4 with doors 101 and 102 being selectively openable and closeable to isolate an individual animal upon the scale 4.

The weight of the individual animal is supplied to an analysis facility 6, for further processing. The individual animals are then sequentially moved to an animal whole body analyzer 5, and the animal can be isolated there by selective opening and closing of doors 103 and 104. The analyzer 5 includes a radiation detector for detecting a radiation level in the animal. The radiation level is then supplied to the analysis facility 6, wherein a radiation concentration is determined for each animal.

The radiation concentration is determined as the total radiation detected divided by the weight of the animal itself. Thus, a radiation concentration can be determined in units of radiation per gram of animal tested. A predetermined standard of an unacceptably high radiation concentration is provided for the analysis facility 6, so that cutting gates 7 can be selectively actuated by signals supplied from the analysis facility 6 to determine whether an individual animal is supplied to an area 9 for "accepted" animals and also, to, an area 10 for "rejected" animals, or to an area 8 for "suspected" animals.

Animals supplied to the area 8 for "suspected" animals are to be further tested, possibly using substantially longer radiation detection times than that originally used in the analyzer 5. Such longer detection times would be employed for animals falling at or near the predetermined cutoff concentration for unacceptably high concentrations.

The animal processing system is designed in a manner that allows high throughput in the monitoring area. A scale 4 is provided to determine the weight of each animal. The analyzer 5 includes mainly gamma detectors, a shield and a multi-channel analyzer (MCA).

Figure 2:
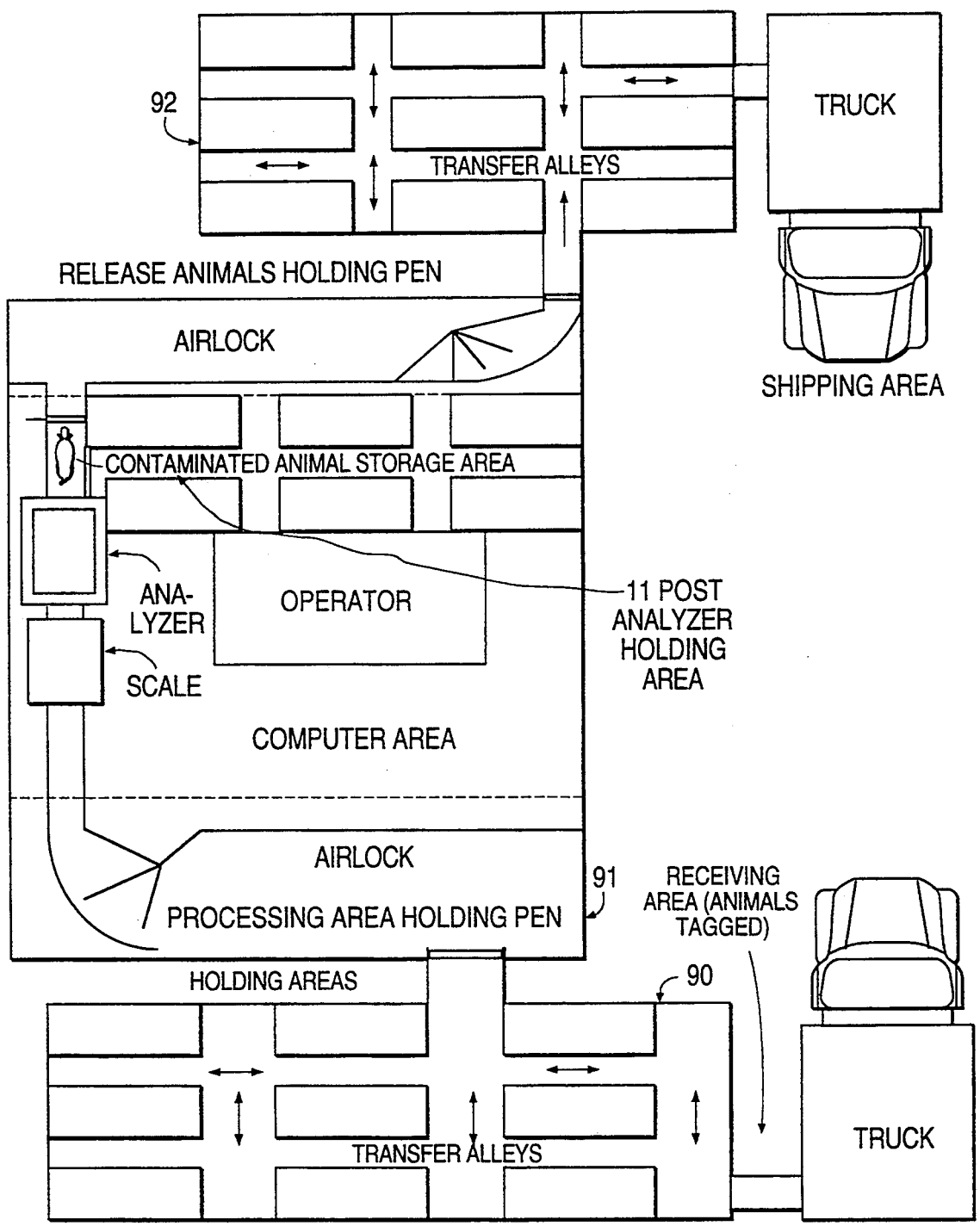
FIG. 2 is a schematic view of the system shown in FIG. 1, together with a complete transfer system from a receiving area all the way through a shipping area to illustrate possible flow patterns.
Figure 3:
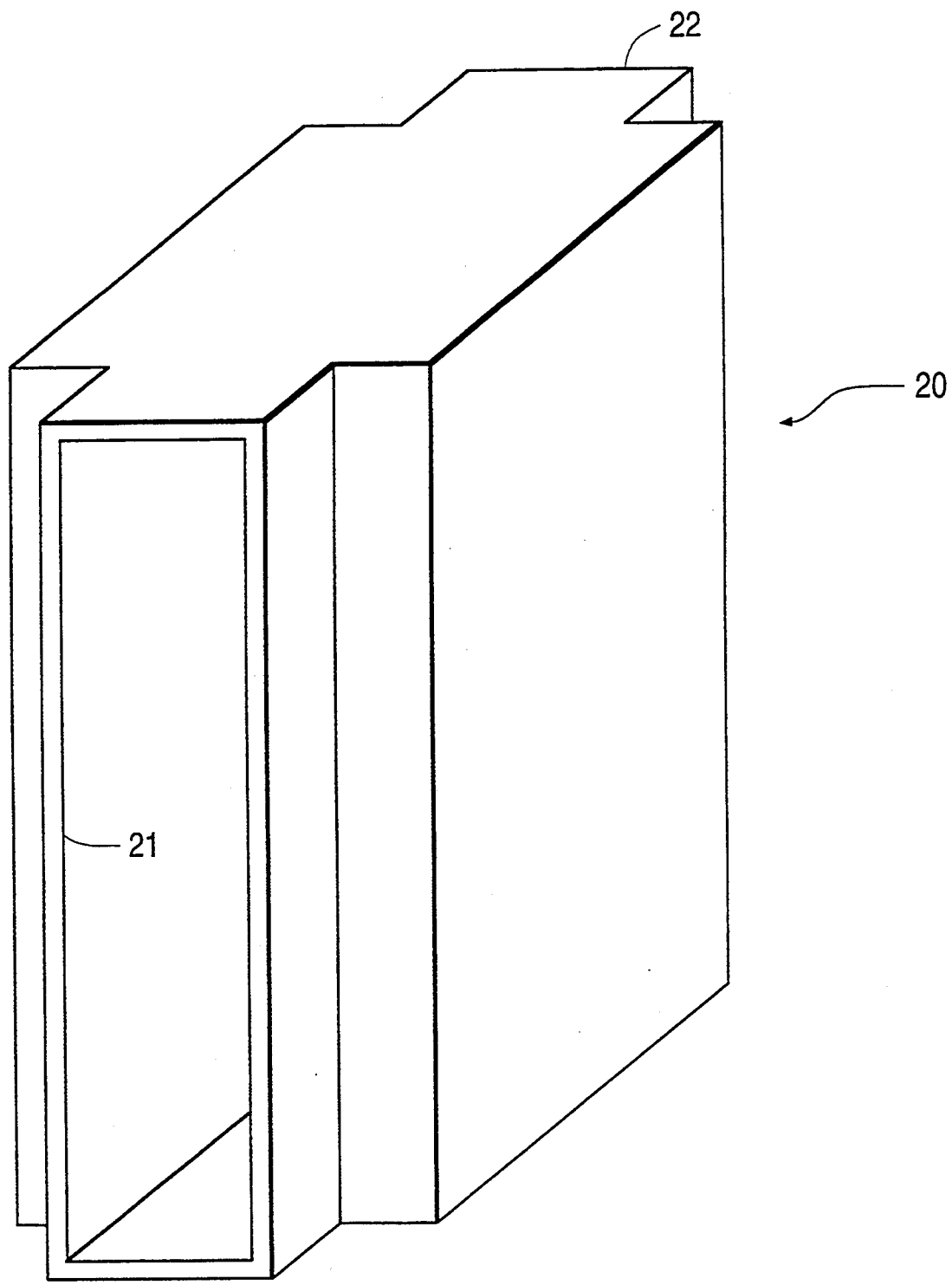
FIG. 3 is a perspective view of an analyzer shield according to the present invention.
Figure 5:
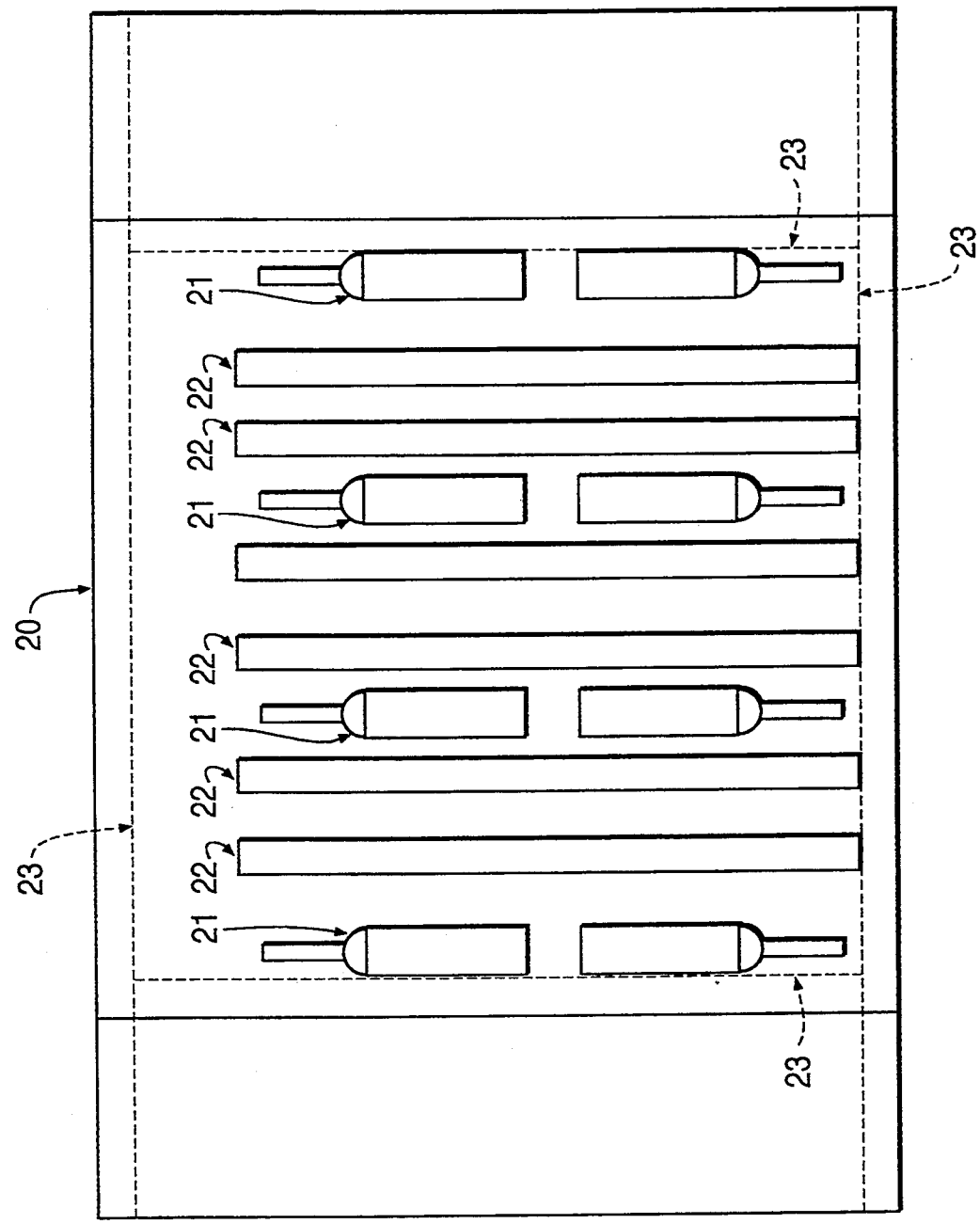
FIG. 5 is a side view of the radiation monitoring system.
Figure 6:
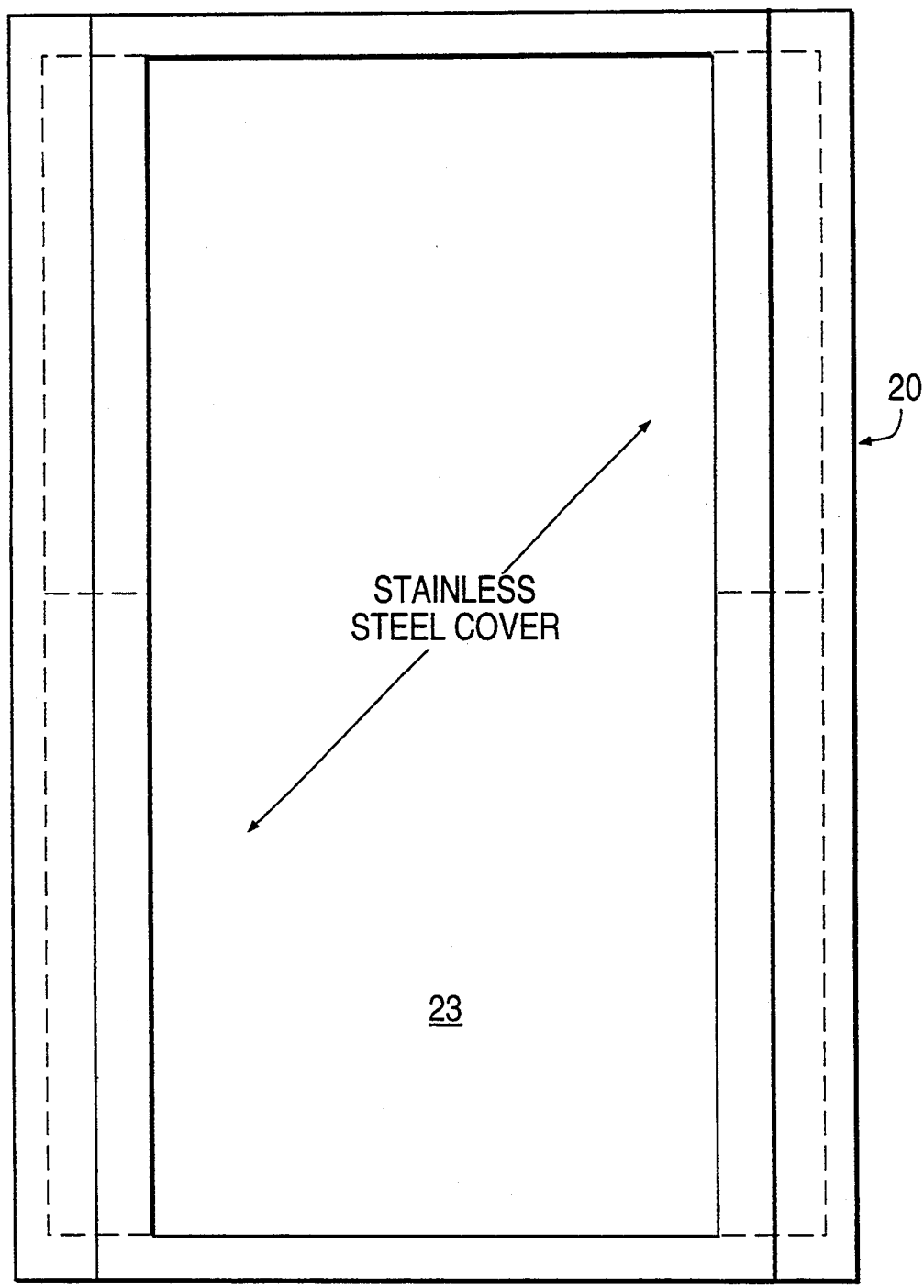
FIG. 6 is an end elevational view of the analyzer shield of FIG. 3.

FIG. 2 is a schematic view illustrating a receiving area 90, an analyzing area generally indicated by block 91, and a released animal holding pen 92. The analyzer area generally includes an air lock, processing area, a holding pen, a computer area, an operator area, an analyzer area including the scale 4 and the analyzer 5, a contaminated animal storage area and an output airlock. This figure merely illustrates one of many possible alternative arrangements of the system which includes the functional units described above. FIGS. 3, 5, and 6 illustrate, respectively, a perspective view, a side view and an end view of an analyzer shield 20 according to the present invention. The shield 20 has a first opening 21 and a second opening 22 therein. The analyzer shield surrounds the squeeze shoot (or crowding shoot) 3 to confine an animal within an area of approximately 1 meter by 2 meters for detector efficiency, while the animal's radiation is counted, the shield 20 is preferably composed of 10 centimeters thick steel plate weighing approximately 53,600 pounds. The interior of the shield 20 is preferably lined with a stainless steel sheet material sealed to the walls to provide a waterproof barrier for protection of the detectors from the debris caused by the animals movements and the animal's activity within the counting area.

Figure 4:
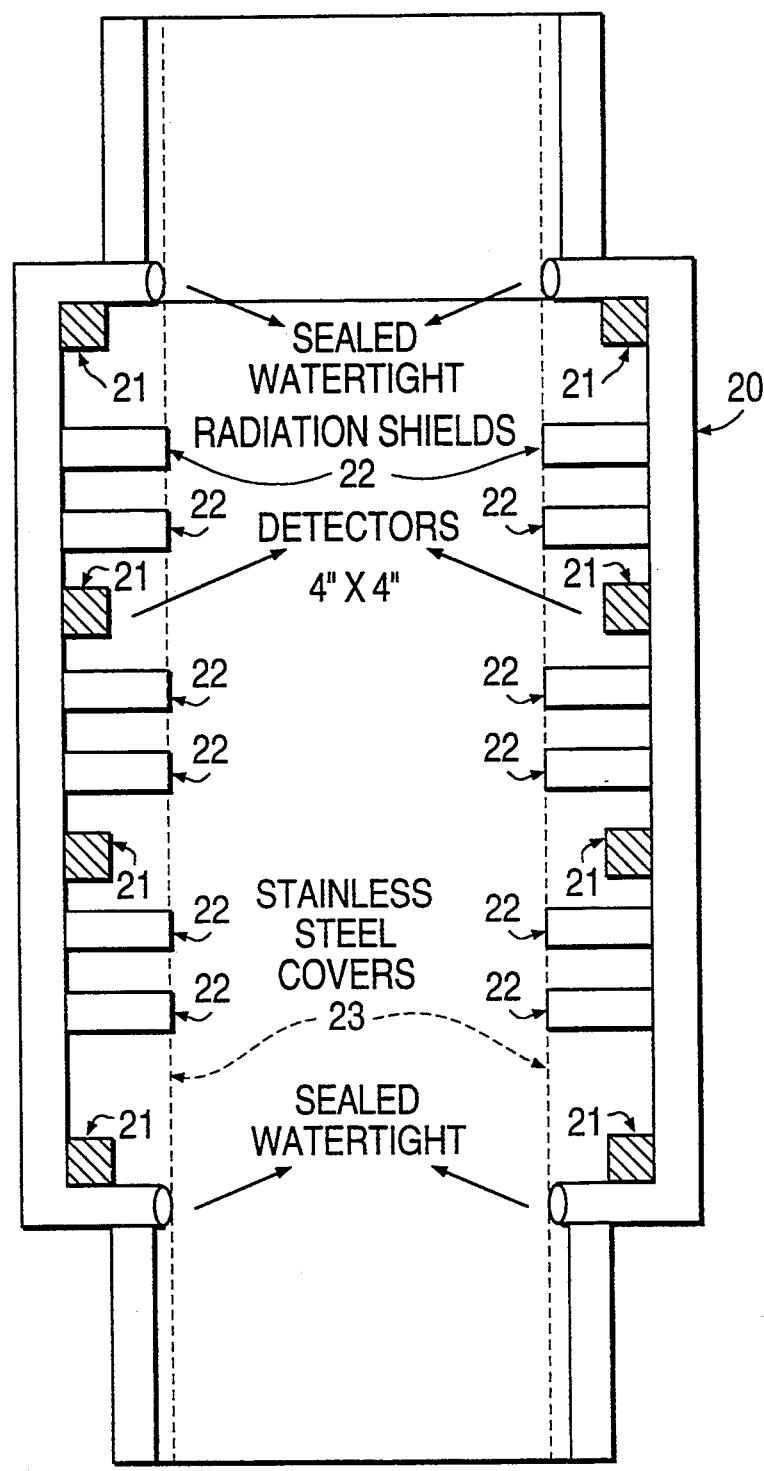
FIG. 4 is a top elevational view of a floor plan of the radiation monitoring system.

A floor plan of the disposition of the radiation detectors and shields is illustrated in FIG. 4. Here, the shield 20 is seen generally in section view with a plurality of radiation detectors 21 disposed in pairs on opposite sides of the shield 20, at a total of eight locations therein. Disposed between adjacent pairs of detectors are a plurality of radiation shields 22 for detection accuracy. A pair of stainless steel covers 23, 23 are illustrated in dotted outline in FIG. 4 for protecting the radiation detectors 21 from moisture and from activity of the animals as discussed above.

Figure 7:
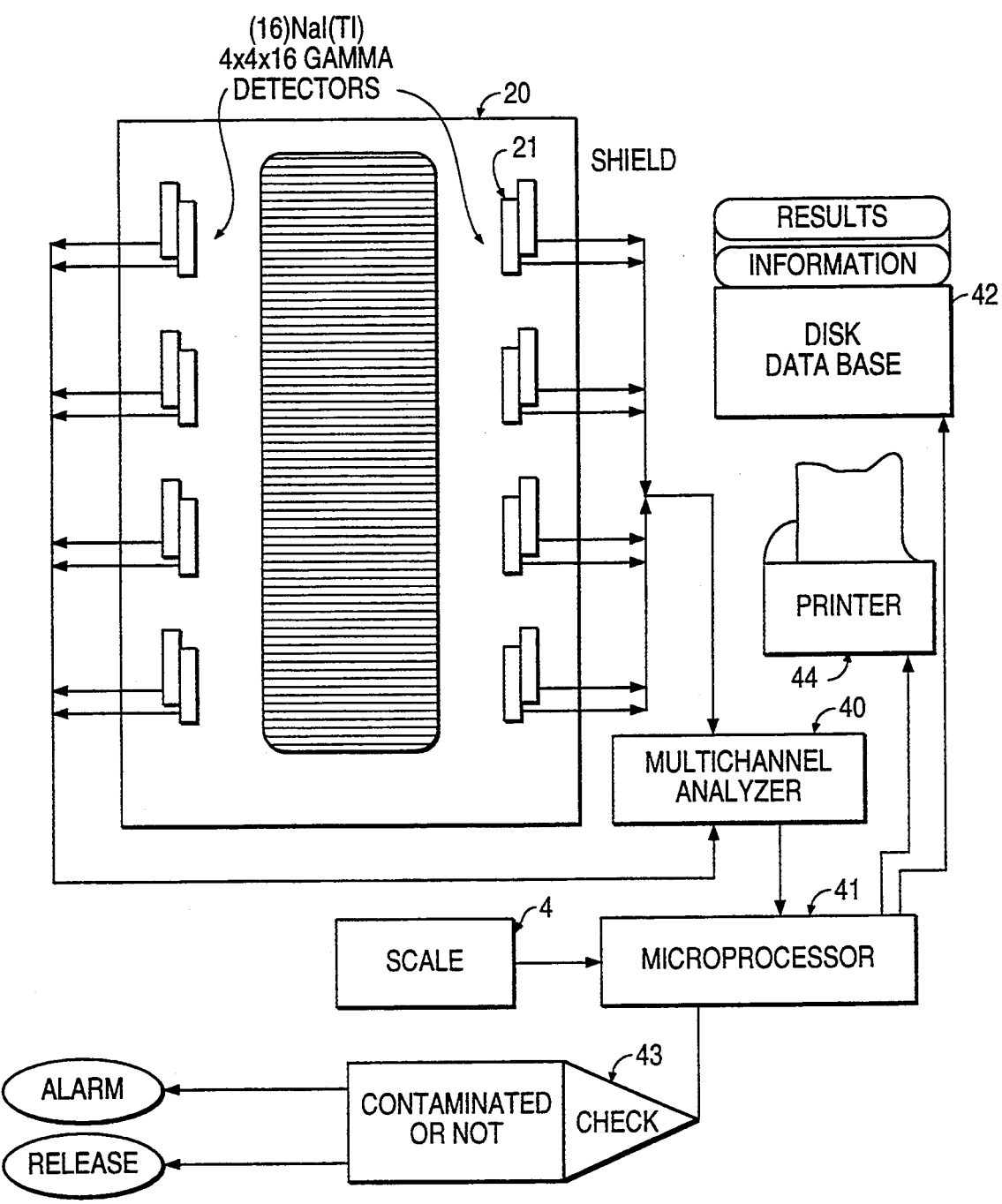
FIG. 7 is an analyzer configuration shown schematically.

FIG. 5 as discussed above, includes a schematic illustration of the radiation detectors 21 in the shield 20, with the shield 20 being broken away and the detectors 21 being schematically indicated. FIG. 7 illustrates the analyzer configuration according to the present invention, schematically illustrating the shield 20 and detectors 21 therein, with the information flow path from the detectors 21 to a multi-channel analyzer 40. The multi-channel analyzer 40 supplies signals to a microprocessor 41. The microprocessor 41 receives signals from the scale 4 as well, and supplies an output signal to a data base 42. The microprocessor 41 determines, as schematically indicated at 43, whether the radiation level (that is, the radiation detected divided by the weight of the animal) exceeds a predetermined level. This predetermined level determines whether the animal is "contaminated" or not by the safety standards chosen by the user, or else as determined by a governmental body. If the animal is contaminated, an alarm can be made to sound, and if the animal is not contaminated, it can be released. The microprocessor 41 also supplies an output signal to a printer in a preferred embodiment, although such printer can be omitted if necessary.

Figure 8:
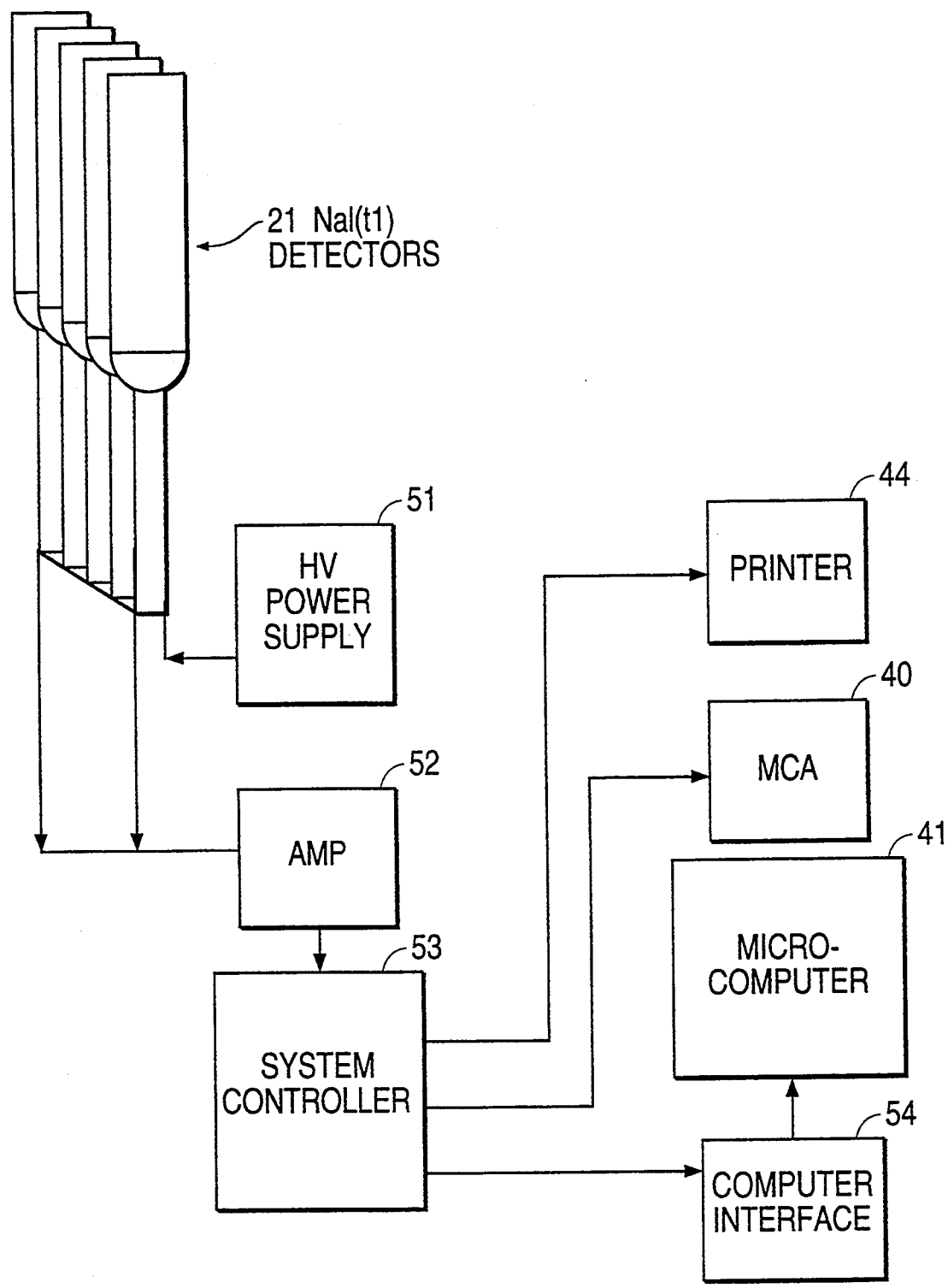
FIG. 8 is a schematic illustration of a detector-computer configuration.

FIG. 8 shows a detailed perspective view of gamma detectors 21 which are NaI(Tl) logs with 3 inch phototube voltage dividers and preamps. A power supply 51 supplies the detectors 21, the amplifier 52 receives signals from the detectors and supplies them to a system control 53. The controller 53 in turn supplies signals to the printer 44, the analyzer 40, and to a computer interface 54. The interface 54 then supplies signals to the microcomputer 41.

Figure 9:
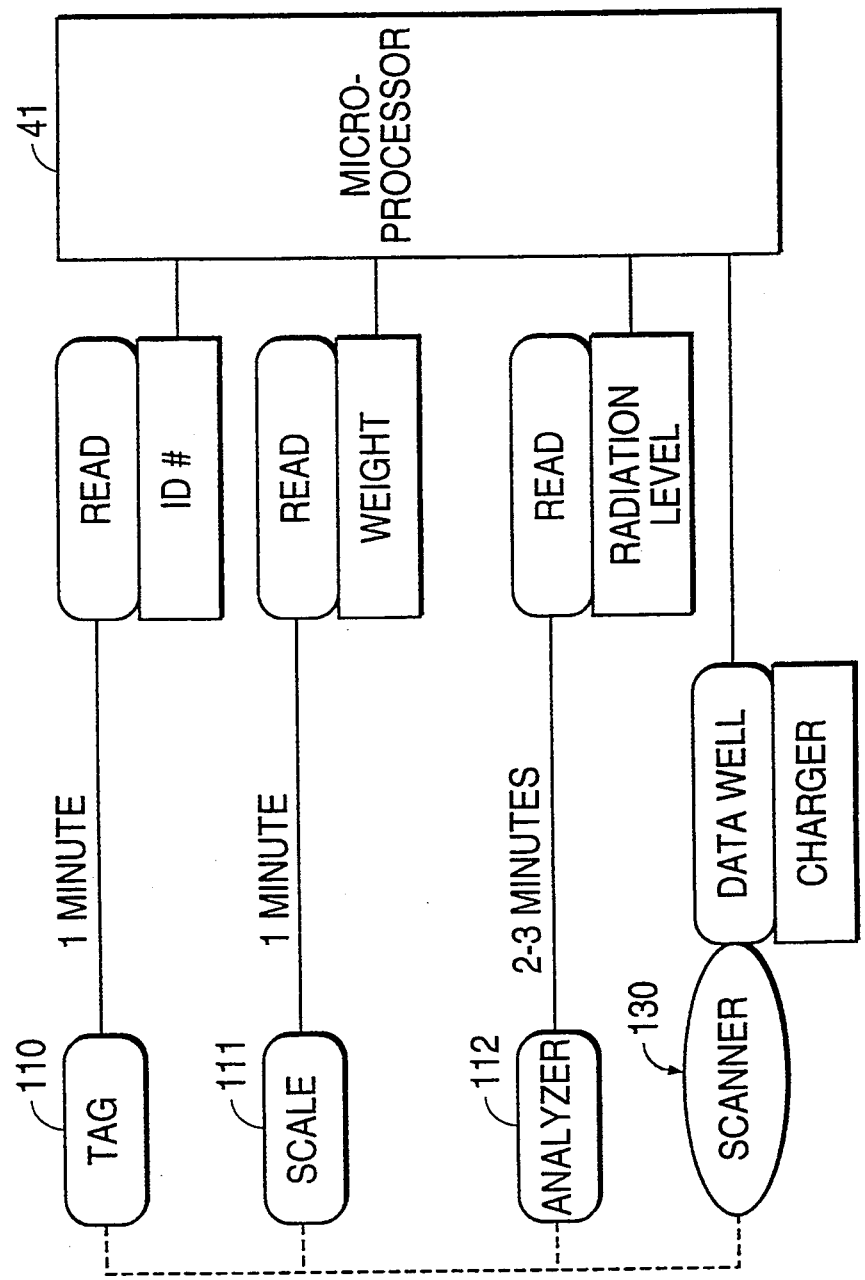
FIG. 9 illustrate input data highways.

FIG. 9 illustrates various operations, and the general preferred time periods involved, according to the present invention. In a first step, an animal is tagged as indicated at 110, an operation taking approximately 1 minute. The tag identification number is read, preferably by a bar code scanner or the like, and this information is then supplied to the microprocessor 41. Similarly, output signals from the scale are supplied to the microprocessor 41, an operation taking approximately 1 minute. The radiation analyzer is operated as indicated at 112. The analyzer is operated for preferably two to three minutes, and this signal is then supplied to the microprocessor 41. A scanner 130 can be used in conjunction with each of the operations 110, 111, and 112, and preferably has a data well including a charger, which communicates with the microprocessor 41.

Figure 10:
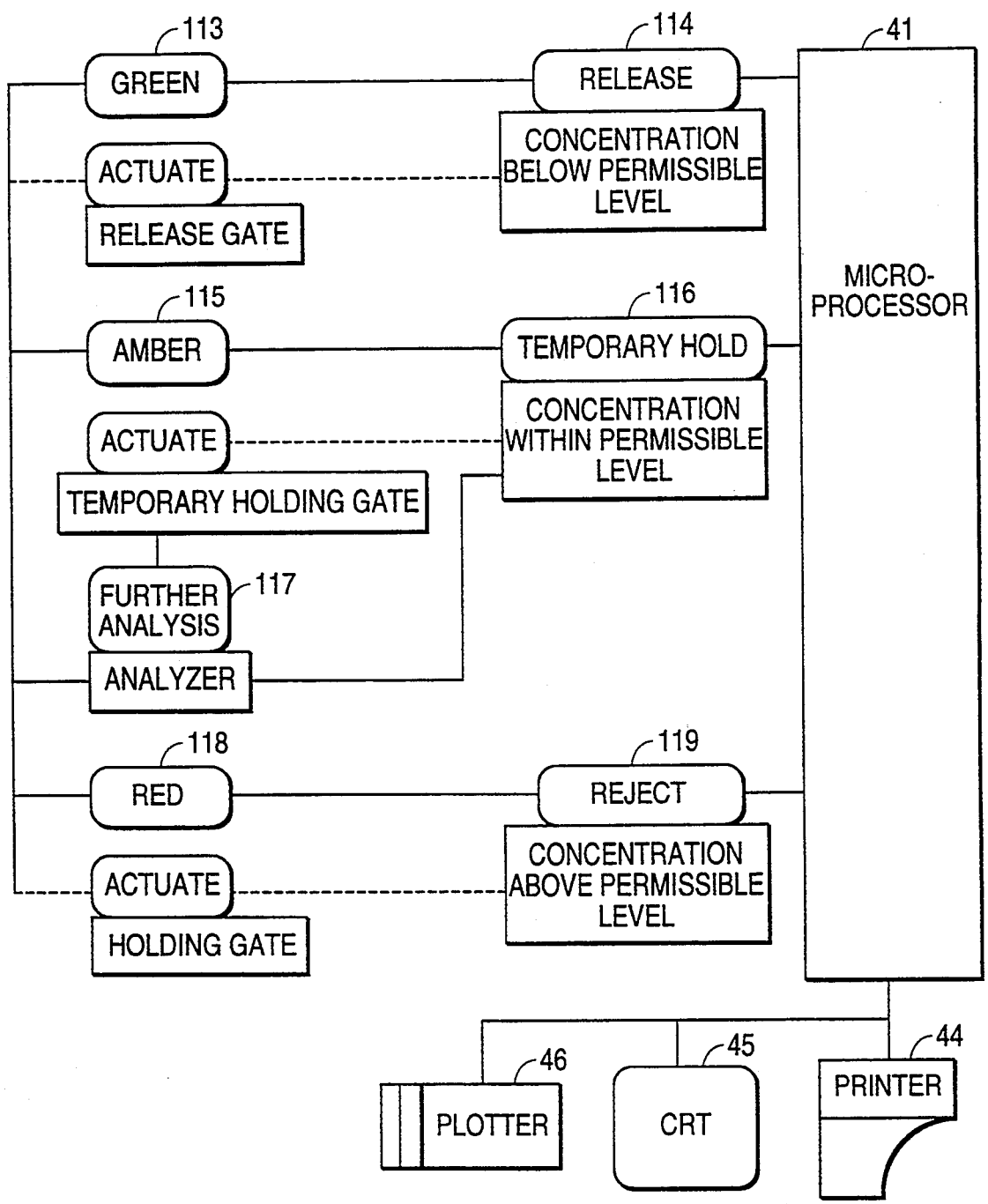
FIG. 10 illustrates output data highways.

FIG. 10 illustrates output data highways of the monitoring system according to the present invention, including a "green" step 113 which releases the animal at step 114 when the concentration is below the cutoff level. The "amber" condition is indicated at step 115, and causes a temporary hold step 116 to occur when the concentration is still within a permissible level but is relatively high. This leads to further analysis at step 117 to determine whether to reject the animal or not. The "red" step 118 triggers a rejection of the animal at step 119 when the concentration of radiation is above a permissible level. These conditions are signaled to the microprocessor 41, which in turn communicates with the printer 44, a CRT display 45 or a plotter 46.

Figure 11:
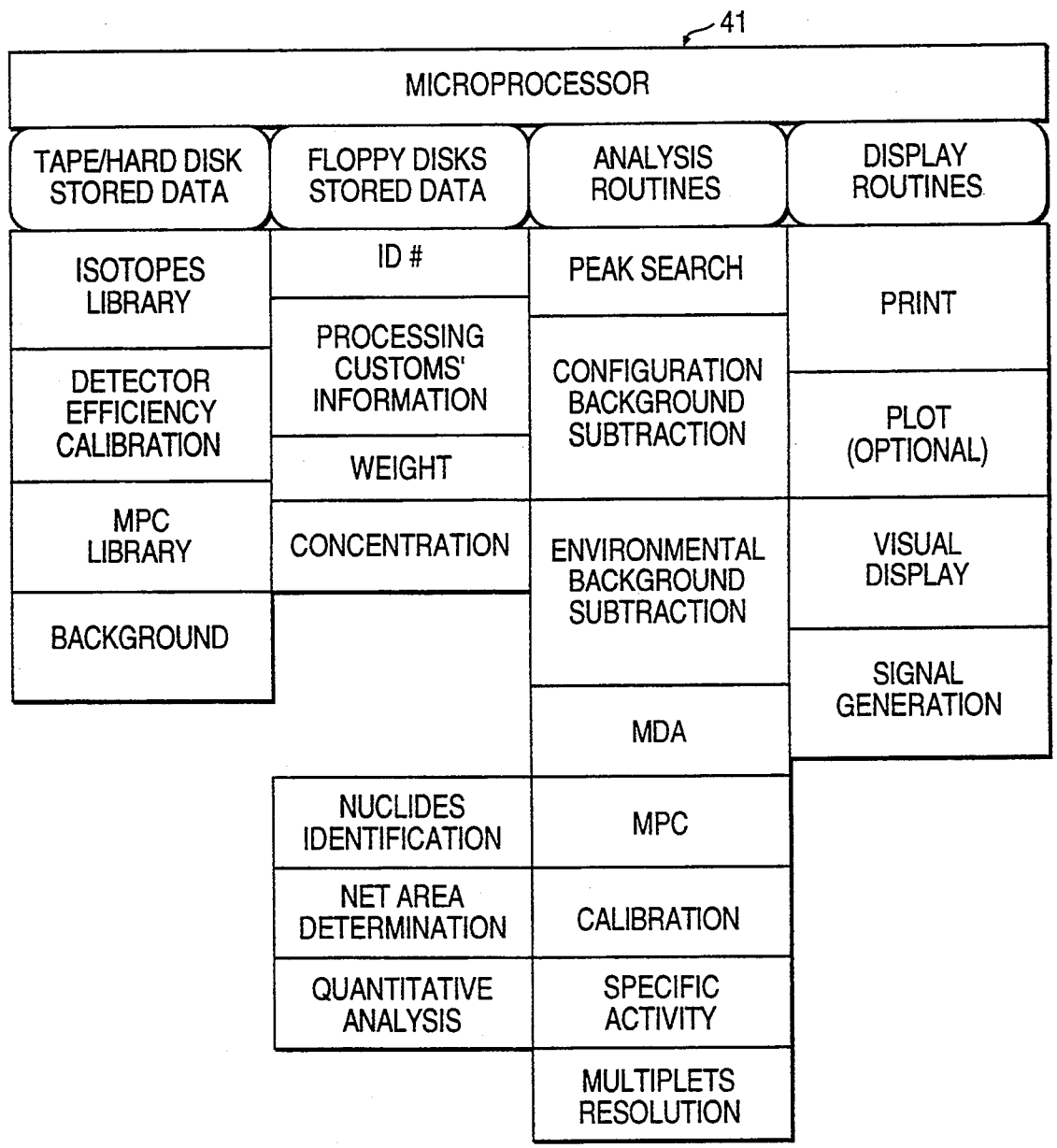
FIG. 11 illustrates schematically processing facilities for use with the present invention.

FIG. 11 illustrates processing facilities of the microprocessor in a preferred embodiment of the present invention. The facilities are labeled in boxes, and illustrate the required stored data on hard or floppy disks, analysis routines, and display routines.

Figure 12:
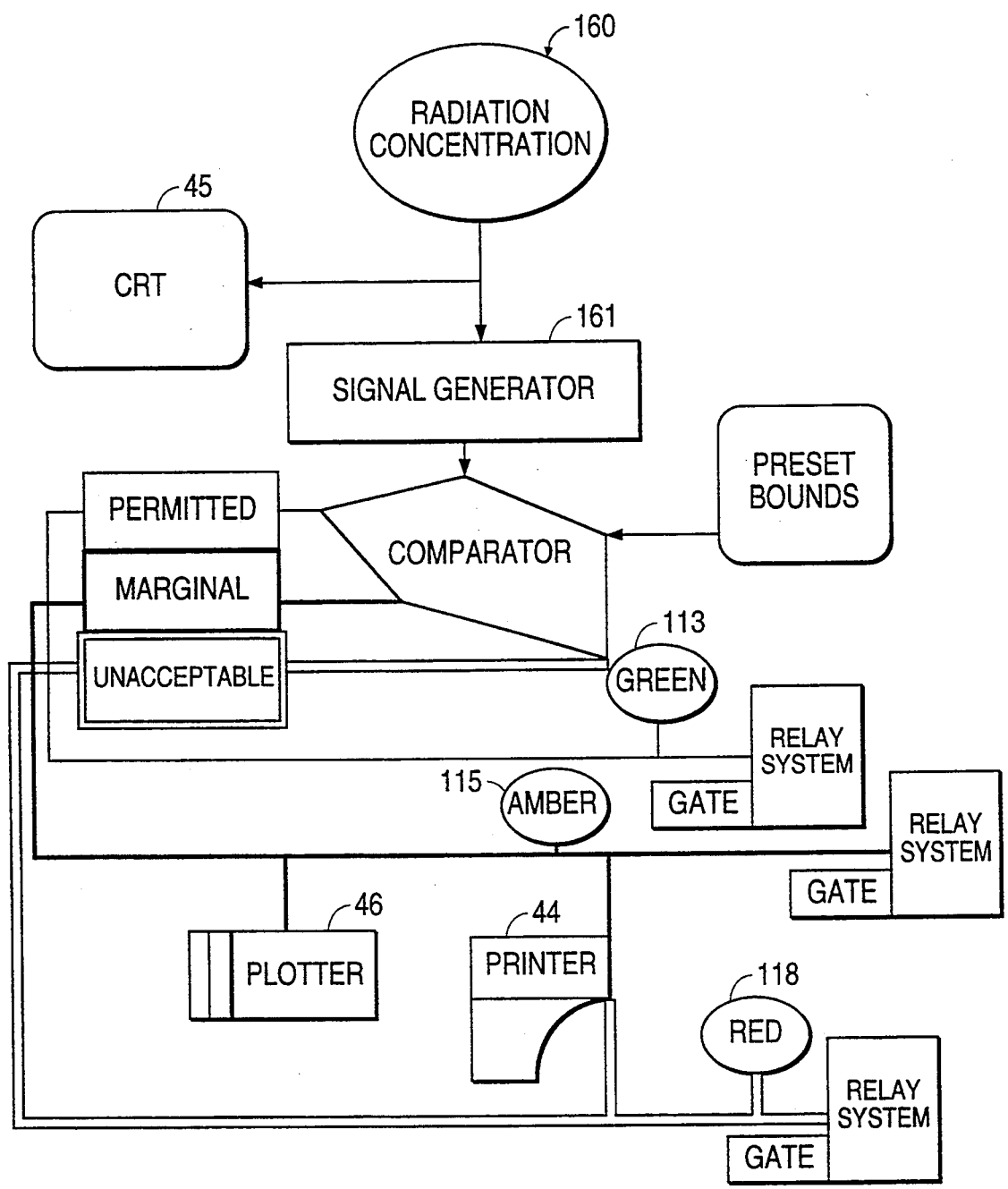
FIG. 12 is a flow chart for indicators.

FIG. 12 schematically illustrates an indicators flow chart of the system according to the present invention. The radiation concentration is determined and supplied as a signal at step 160 to either the CRT 45 or to a signal generator 161. The light colors shown in this figure are in correspondence with that shown in FIG. 10.

Figure 13:
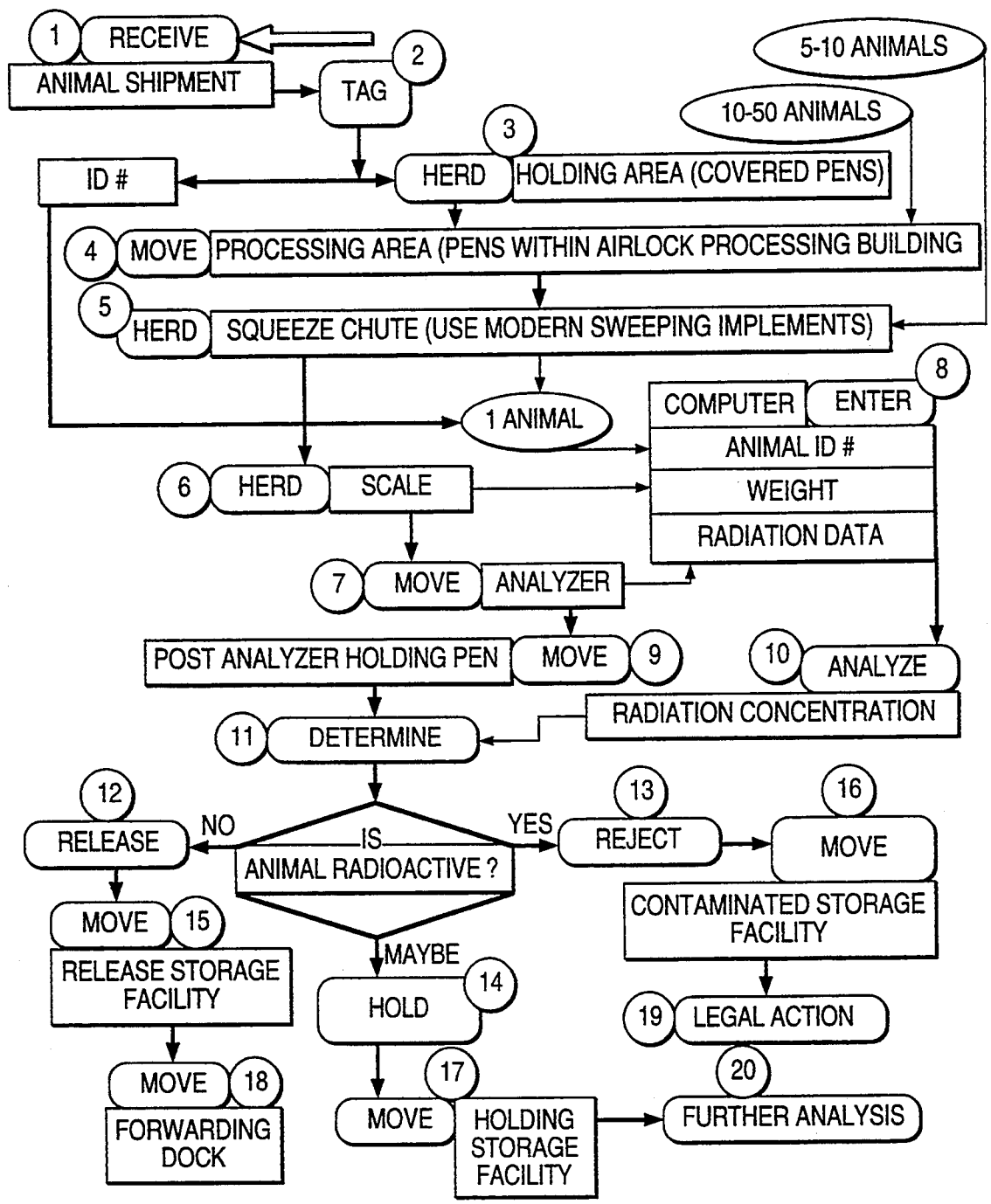
FIG. 13 is a process flow chart.

FIG. 13 illustrates process steps carried out on animals, in accordance with the present invention. The steps are substantially as described hereinabove.

Figure 14:
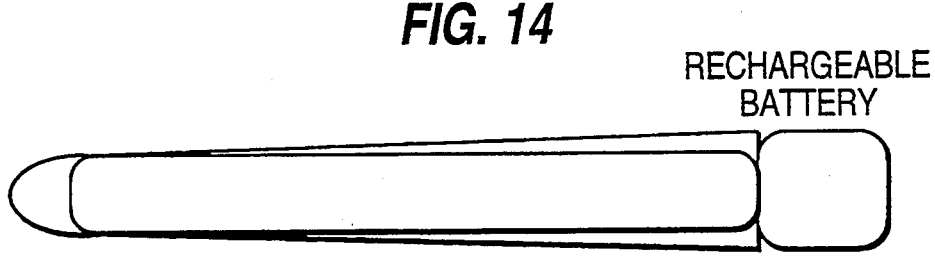
FIG. 14 is an optical bar code scanner illustrated schematically, which is usable with the present invention.

FIG. 14 is a schematic diagram of an optical bar code scanner for use in the present invention. Such scanners are conventional, and any type of bar code or other information scanner is usable in conjunction with the present invention.

Figure 15:
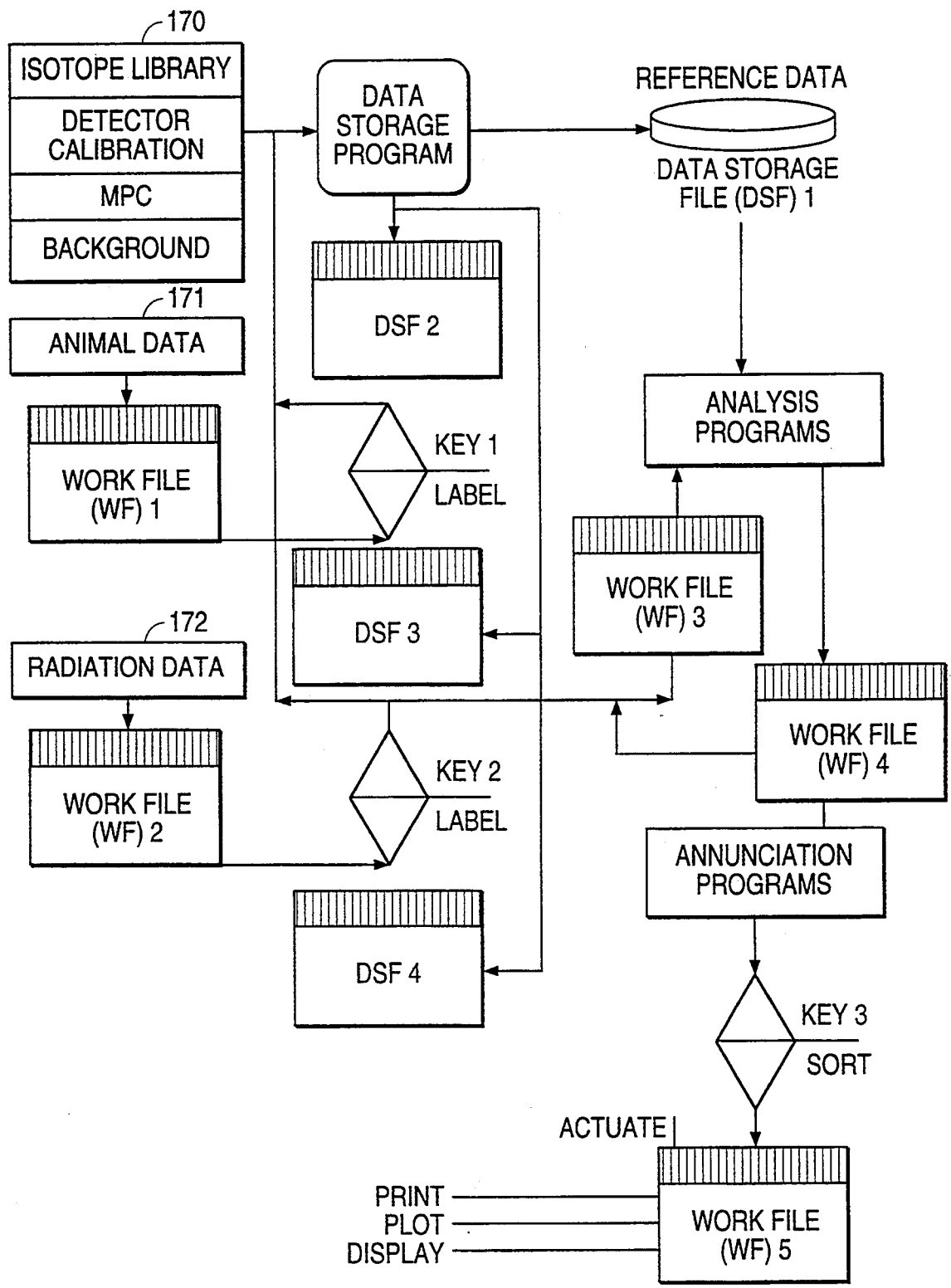
FIG. 15 is a schematic diagram of the data processing logic usable with the present invention.

FIG. 15 illustrates data processing logic used in the present invention. Here, an isotope library 170 is provided, as are animal data at 171. Radiation data is supplied at step 172.

Figure 16:
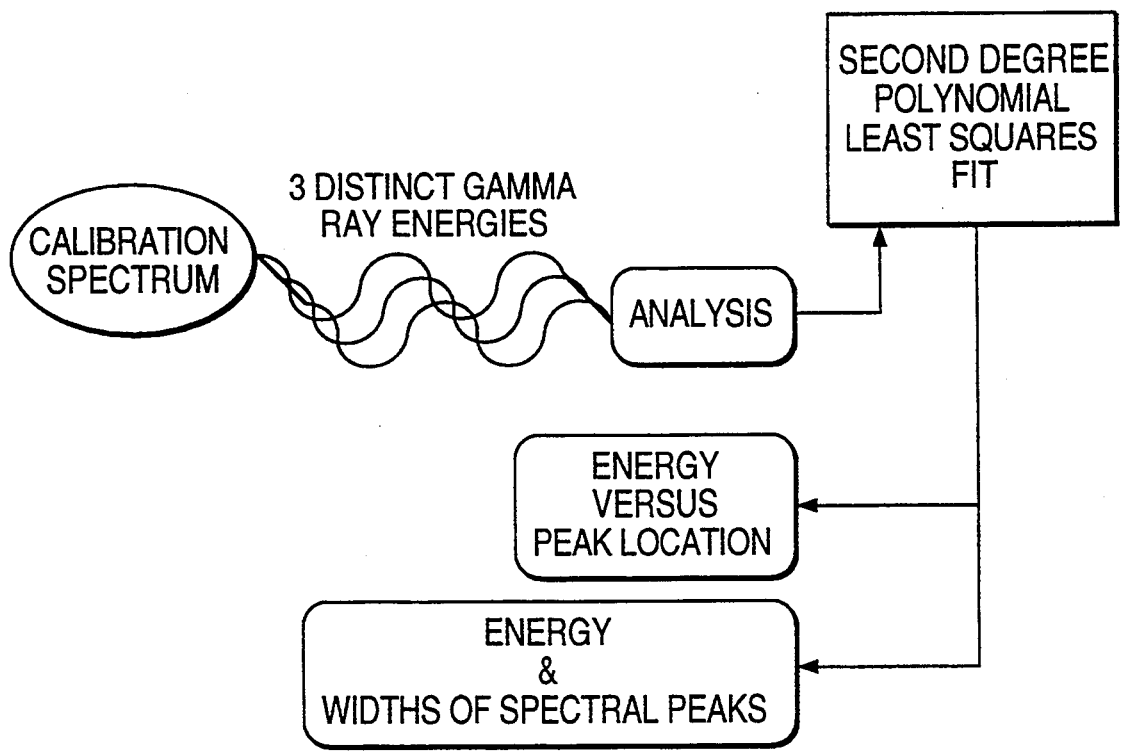
FIG. 16 schematically illustrates energy calibration of detectors.

FIG. 16 illustrates schematically energy calibration of the gamma detectors 21 for the system according to the present invention. The detectors preferably are calibrated according to three distinct gamma ray energies for analysis thereof. The analysis is preferably by a curve fit, and is to determine the energy of the rays versus the peak location as well as the energy of the rays and the widths of the spectral peaks.

Figure 17:
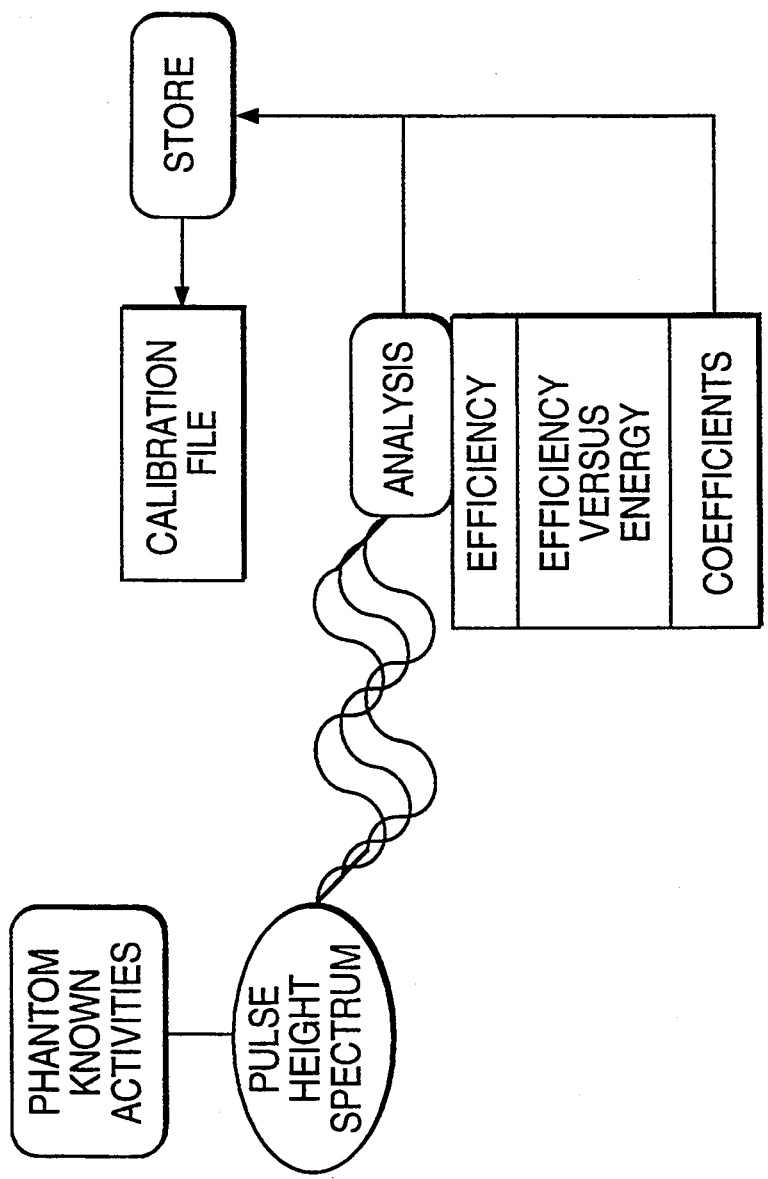
FIG. 17 illustrates frequency calibration of detectors.

FIG. 17 similarly illustrates frequency calibration of the gamma ray detectors 21. Such calibration of detectors is otherwise known in the radiation detection art and need not be further illustrated herein.

Figure 18:
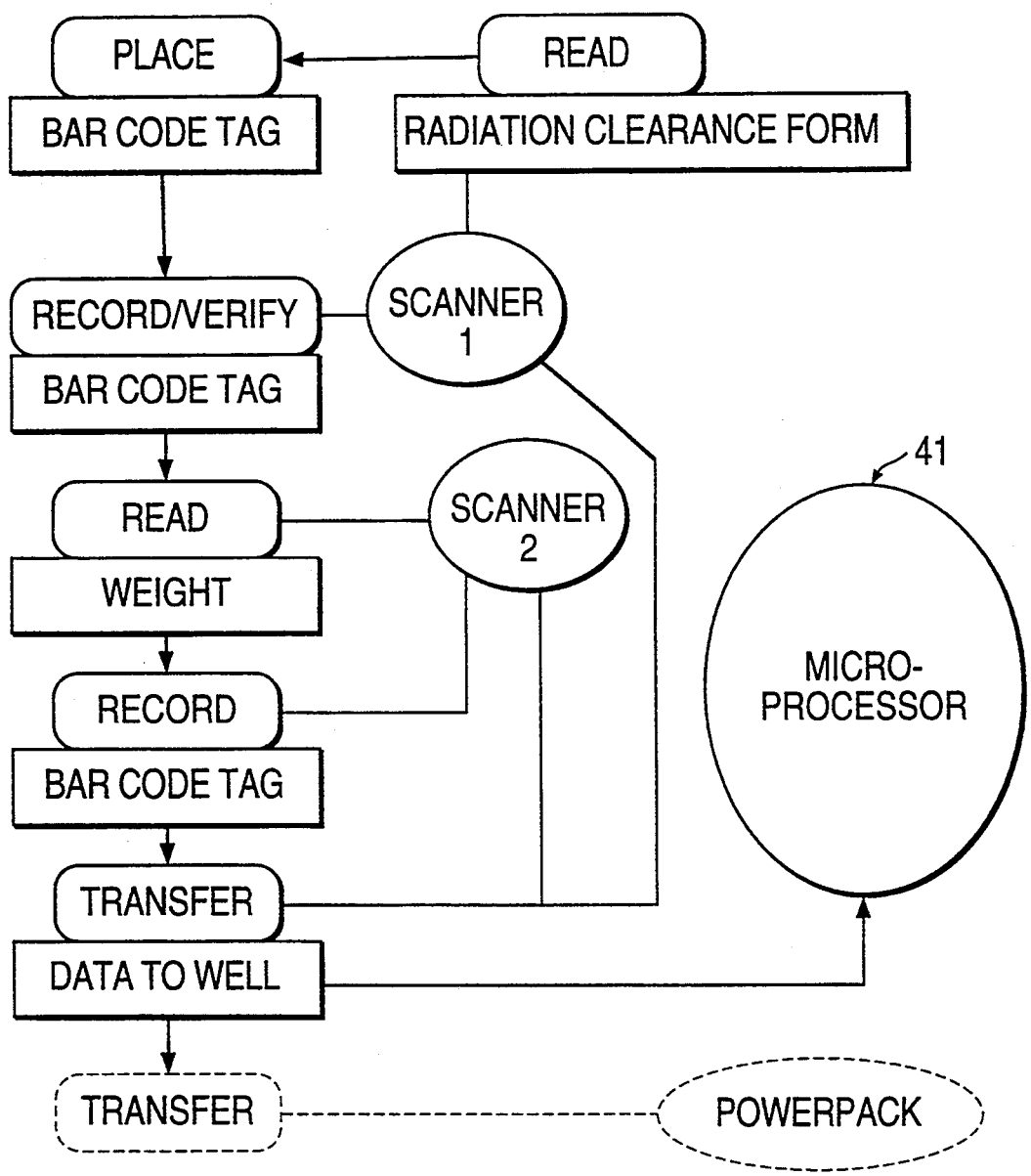
FIG. 18 illustrates schematically a tagging system and bar code use.

FIG. 18 illustrates a tagging system and bar code use for the livestock monitoring system according to the present invention.

Figure 19:
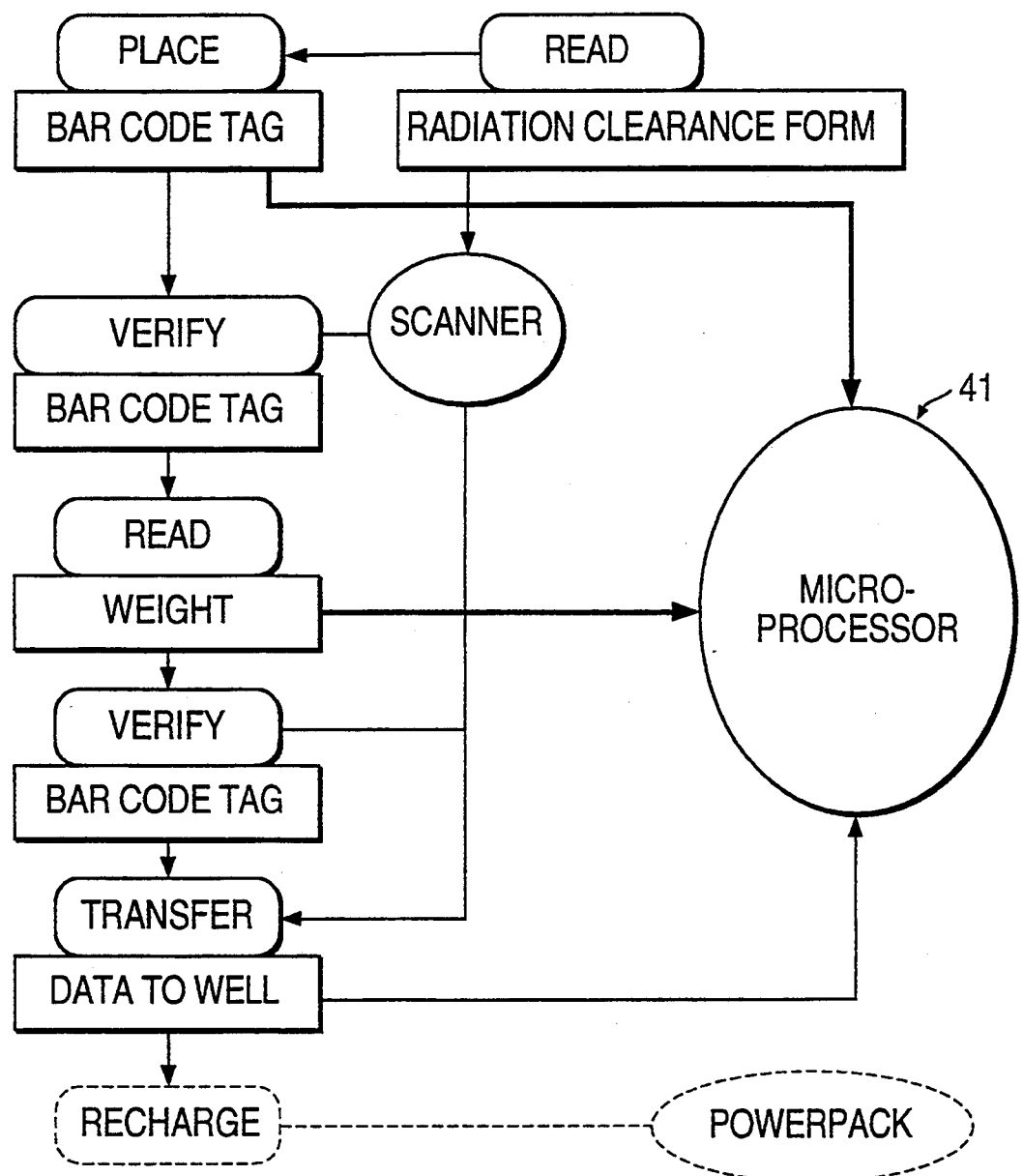
FIG. 19 illustrates an alternative tagging system and bar code use.

FIG. 19 illustrates an alternative tagging system and bar code use. It is contemplated that other tagging systems and automatic readers of codes, including codes other than bar codes, could be used with the present invention, and all such alternative systems are contemplated as being usable with the present invention.

Figure 20:
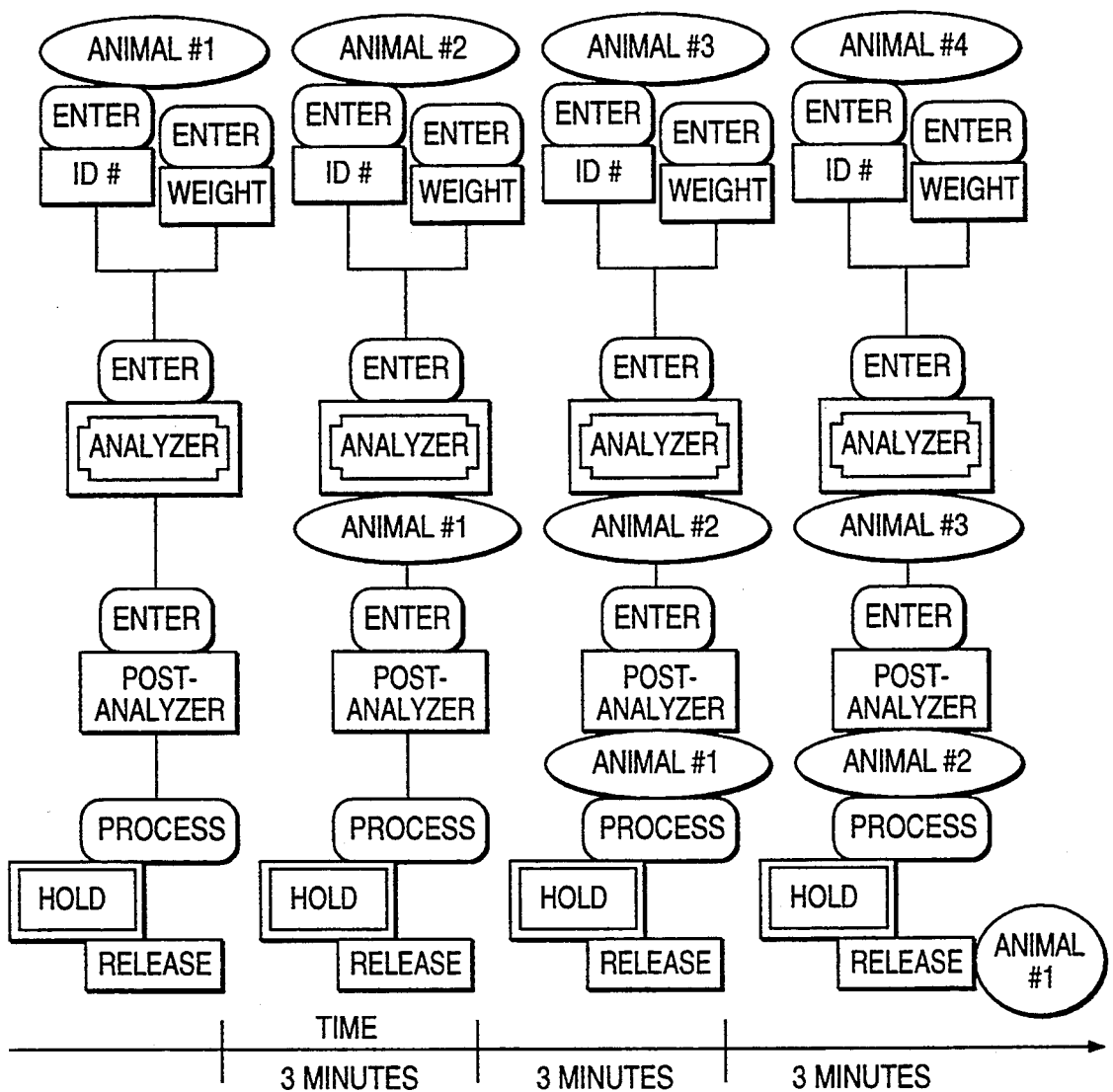
FIG. 20 is a schematic diagram of animal flow.

FIG. 20 indicates animal flow in the system according to the present invention, showing animal information flow paths for animals 1–4.

Figure 21:
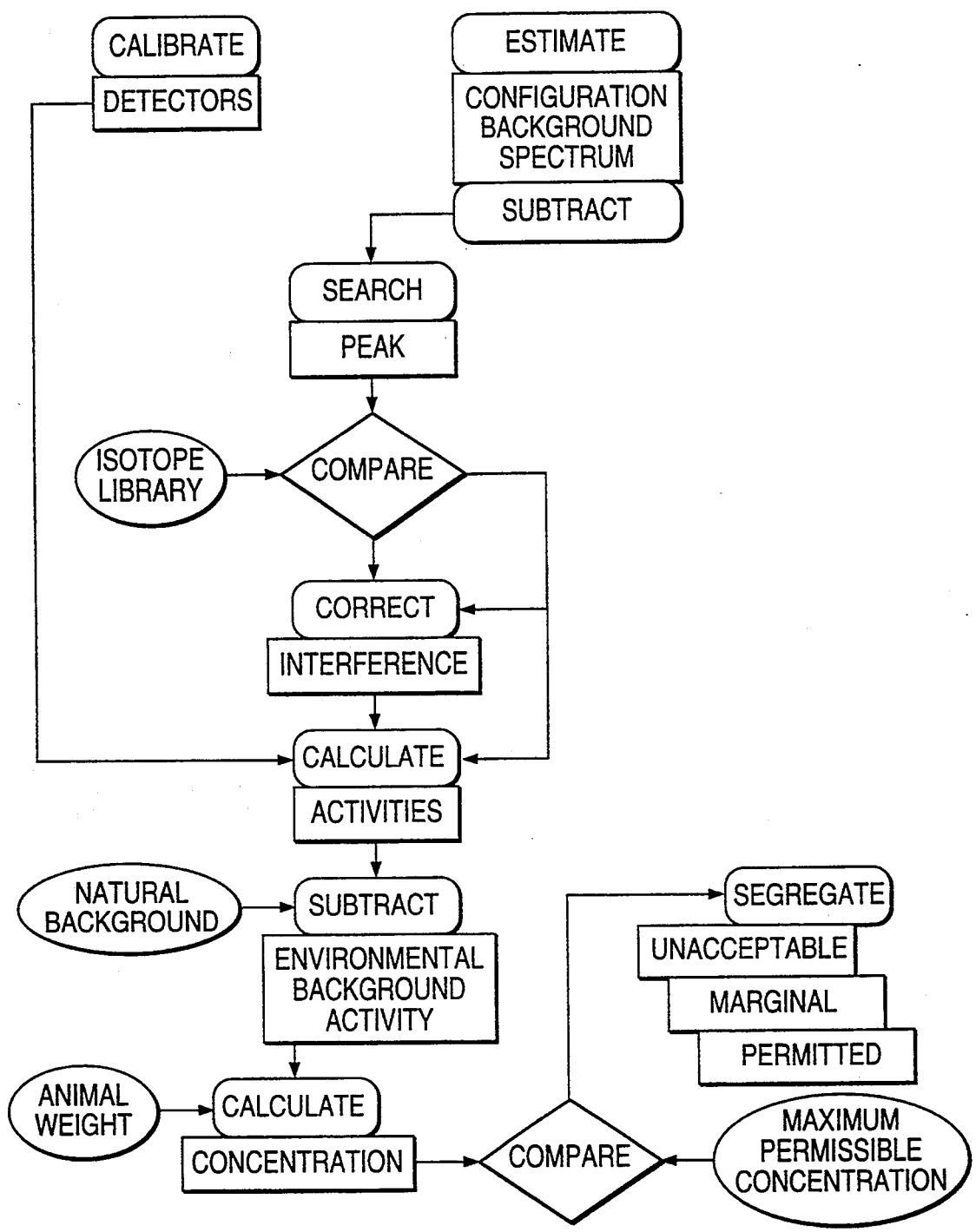
FIG. 21 is a radiation surveillance flow chart for livestock.

FIG. 21 illustrates a radiation surveillance flow chart included detailed operation steps for the detectors according to the present invention.

The livestock whole body radiation monitor of the present invention is designed to detect any traces of radiation contamination in live animals due to contaminated feed or any other radiation pathways. The system is designed to handle a large volume of livestock at a short time without the need for laboratory analysis or quarantine. The radioactively contaminated animal whole body analyzer measures minute amounts of gamma rays being emitted from live animals. It then analyzes this data to determine the kind of radioactive material present and how much of each isotope is present. This sensitive counter can easily detect and measure the natural levels of radioactive K-40 present in the animals (about 400 nCi or $14.8 \times 10^3$ Bq for a cow) and other game emitting radioisotopes of interest which are not naturally occurring. The longer an animal is monitored within the system, the lower will be the detectable limit. For example, for a 3 minute measuring period it is estimated that a total amount of radioactivity of 6 nCi (222 Bq) of Cs-137 can be detected. That is, for a 460 kg cow the lower limit of detection would be about $1.3 \times 10^{-2}$ pCi/g (0.48 B1/kg).

The container radiation monitoring system also is shown, and is designed to detect any traces of radiation contamination in closed crates and large containers without the need for random sampling of contents. The system can also be used for whole body counting of live animals, provided the animals are properly caged. This system too is designed to handle a large volume of containers at a short time without the need for further laboratory analysis.

FIGS. 22-30 illustrate corresponding apparatus and steps similar to that described hereinabove for animals, but with respect to containers.

Figure 22:
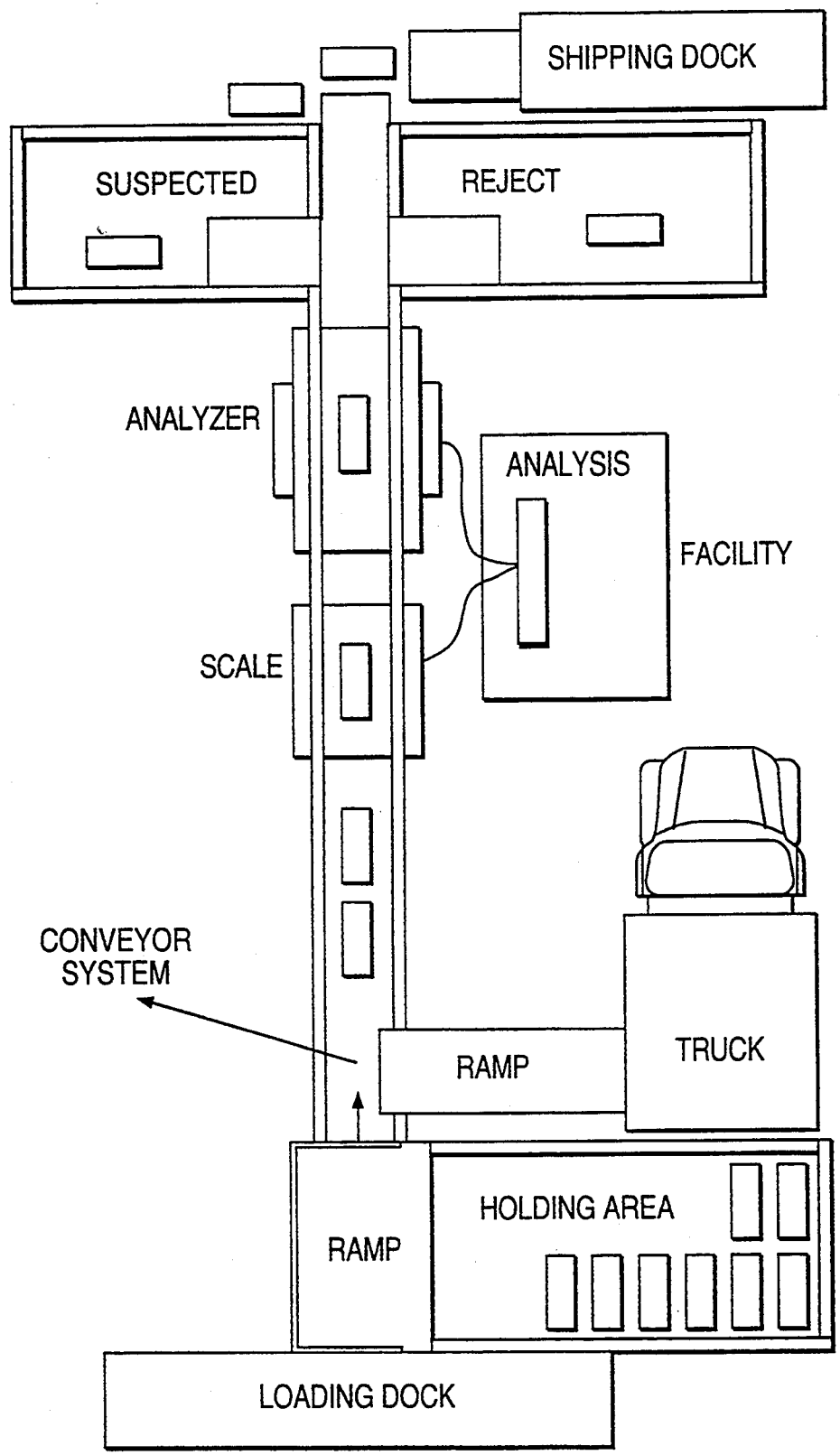
FIG. 22 schematically shows a container radiation monitoring system according to the invention.
Figure 23:
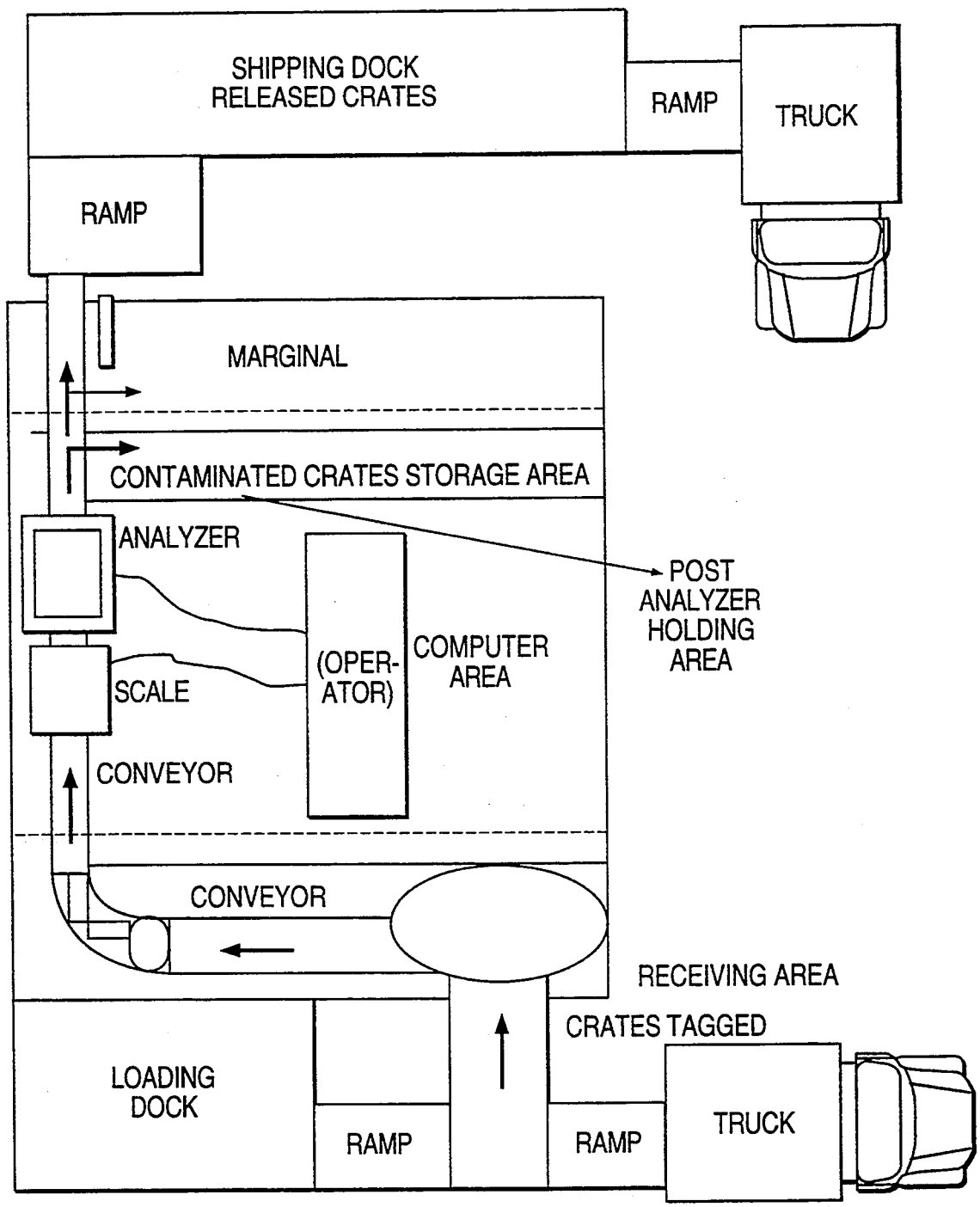
FIG. 23 is a schematic view including the entire flow path from a receiving area to an output shipping area.

FIG. 22 illustrates the scale and analyzer which are similar to FIG. 1, and FIG. 23 illustrates the flow path and handling facilities schematically, similar to that shown in FIG. 2 of the present invention.

Figure 24:
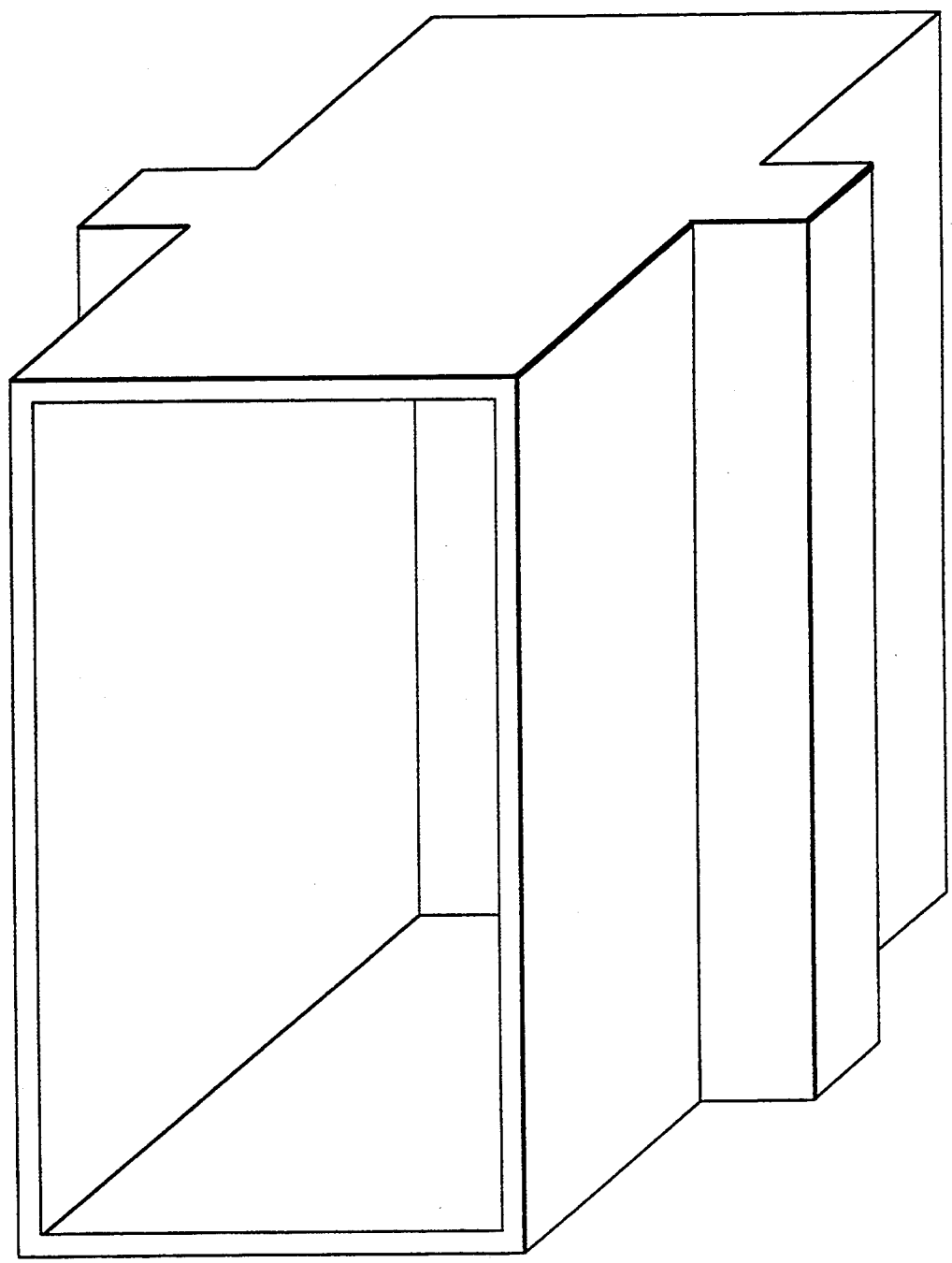
FIG. 24 is a perspective view of an analyzer shield according to the present invention.
Figure 26:
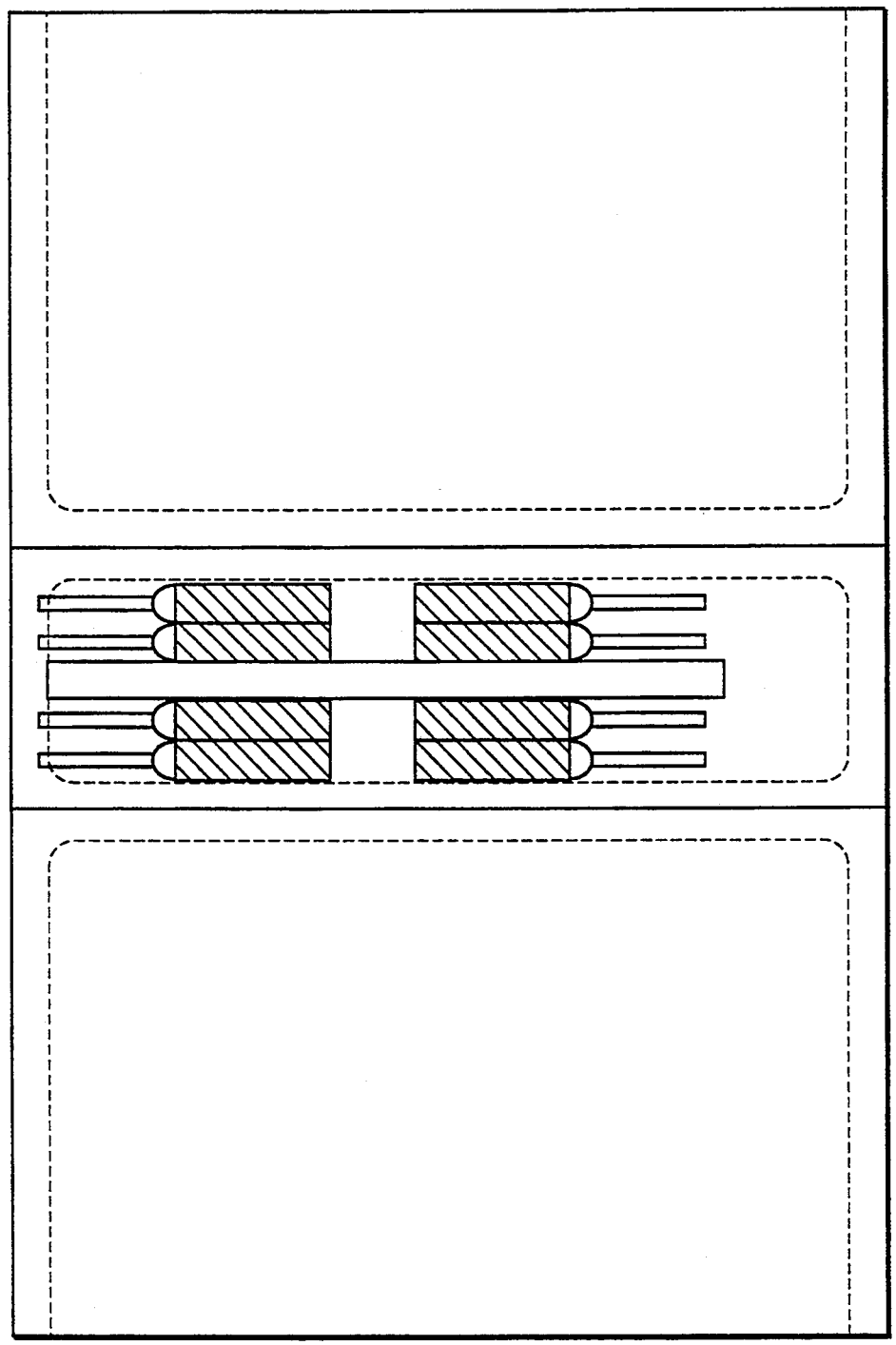
FIG. 26 is a side view of the container radiation monitoring system.
Figure 27:
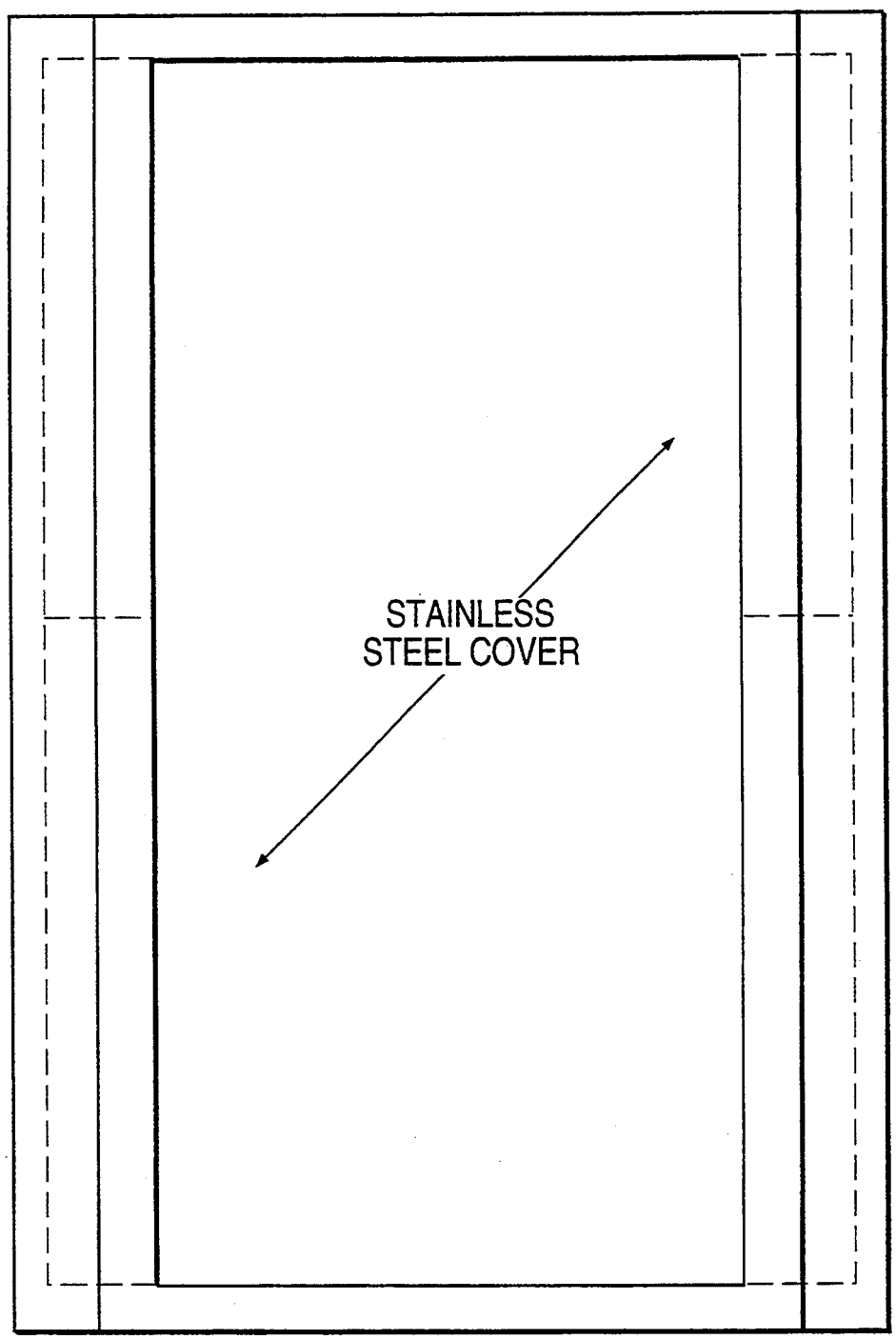
FIG. 27 is an end view of the analyzer shield according to the present invention.

FIGS. 24, 26 and 27 are respectively: a perspective view, side view and end view of an analyzer shield for the container radiation monitoring system. This is substantially identical to that shown in the previously-discussed FIGS. 3, 5 and 6, different proportions being used for the containers according to the present invention.

Figure 25:
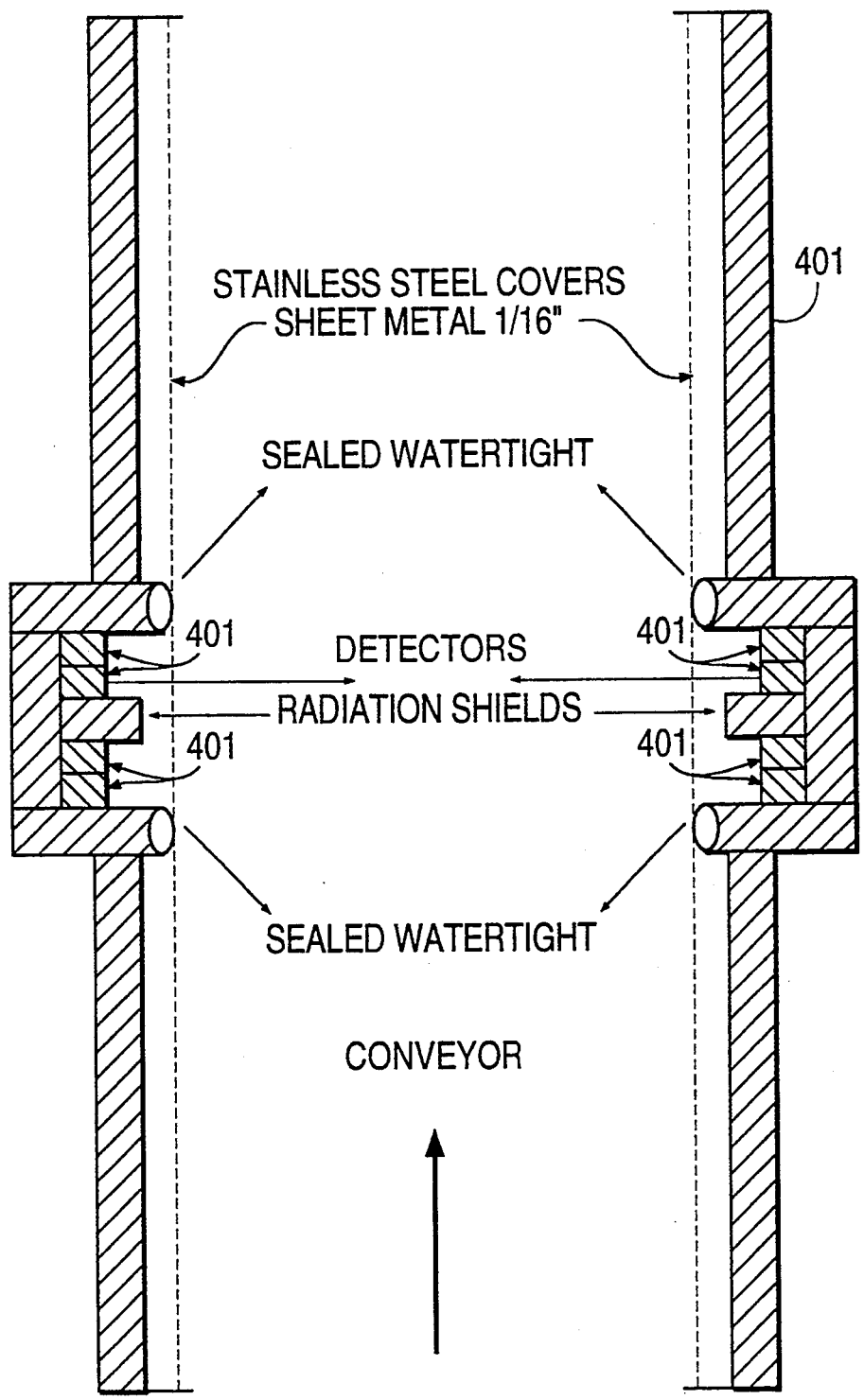
FIG. 25 is an elevational view of a floor plan for the container monitoring system.

FIG. 25 is a floor plan or elevational view of the container radiation monitoring system according to the present invention. Here, four detectors 401 are disposed on each side of the radiation shield 400. These detectors 401 are substantially the same as the detectors 21 described hereinabove, and function in substantially the same way. The calibration and other steps are also substantially as described hereinabove.

Figure 28:
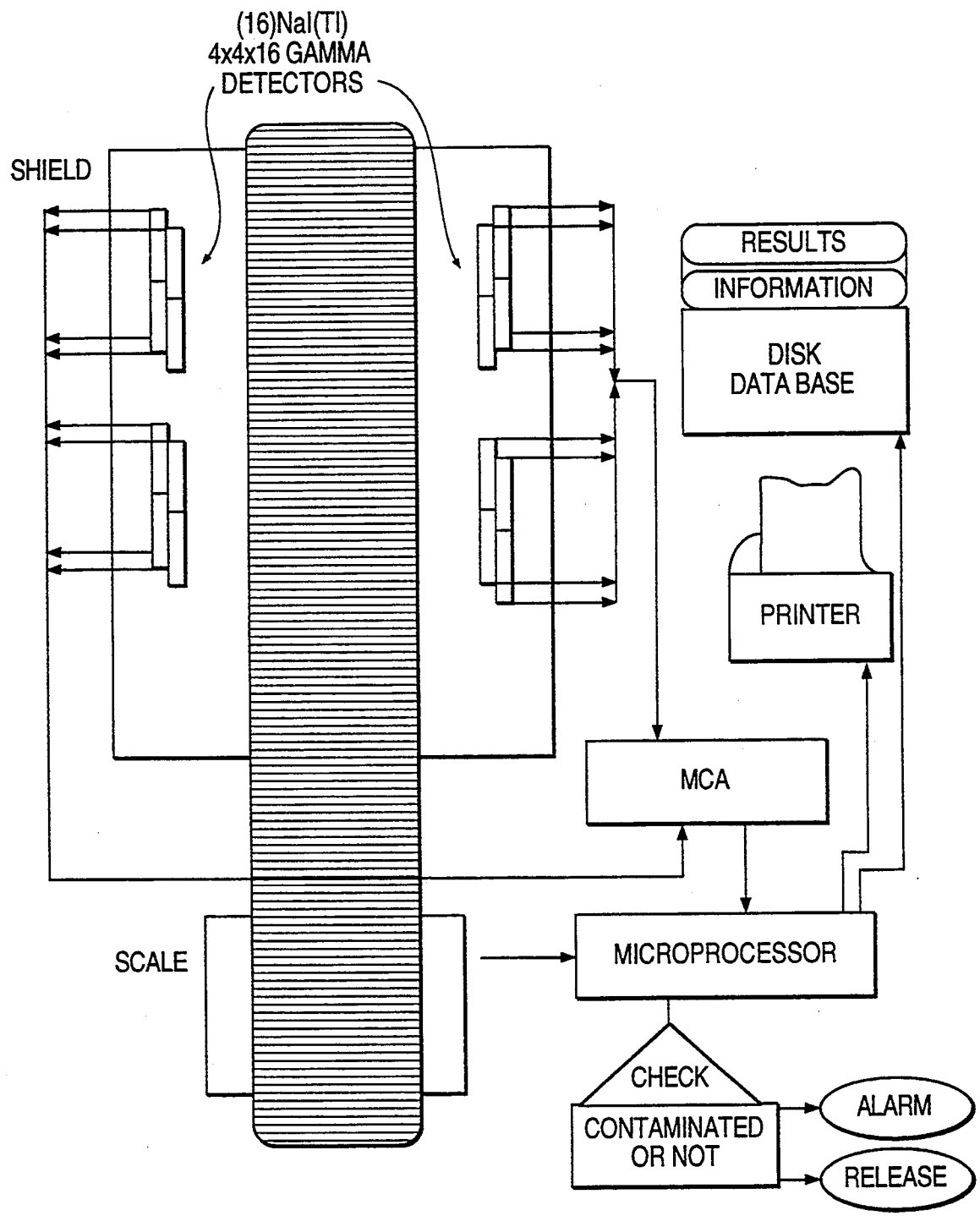
FIG. 28 illustrates an analyzer configuration for the container monitoring system.

FIG. 28 is an analyzer configuration for the container monitoring system according to the present invention. Here, a conveyer is used to move the containers or crates, rather than relying upon the mobility of the animals themselves, as was applied previously to similar FIG. 7 discussed hereinabove.

The input and output data highways of the container monitoring system according to the present invention are substantially as shown in FIGS. 9 and 10 discussed hereinabove. Additionally, FIGS. 11 and 12 also apply to the container monitoring system, and these figures have been discussed in the above.

Figure 29:
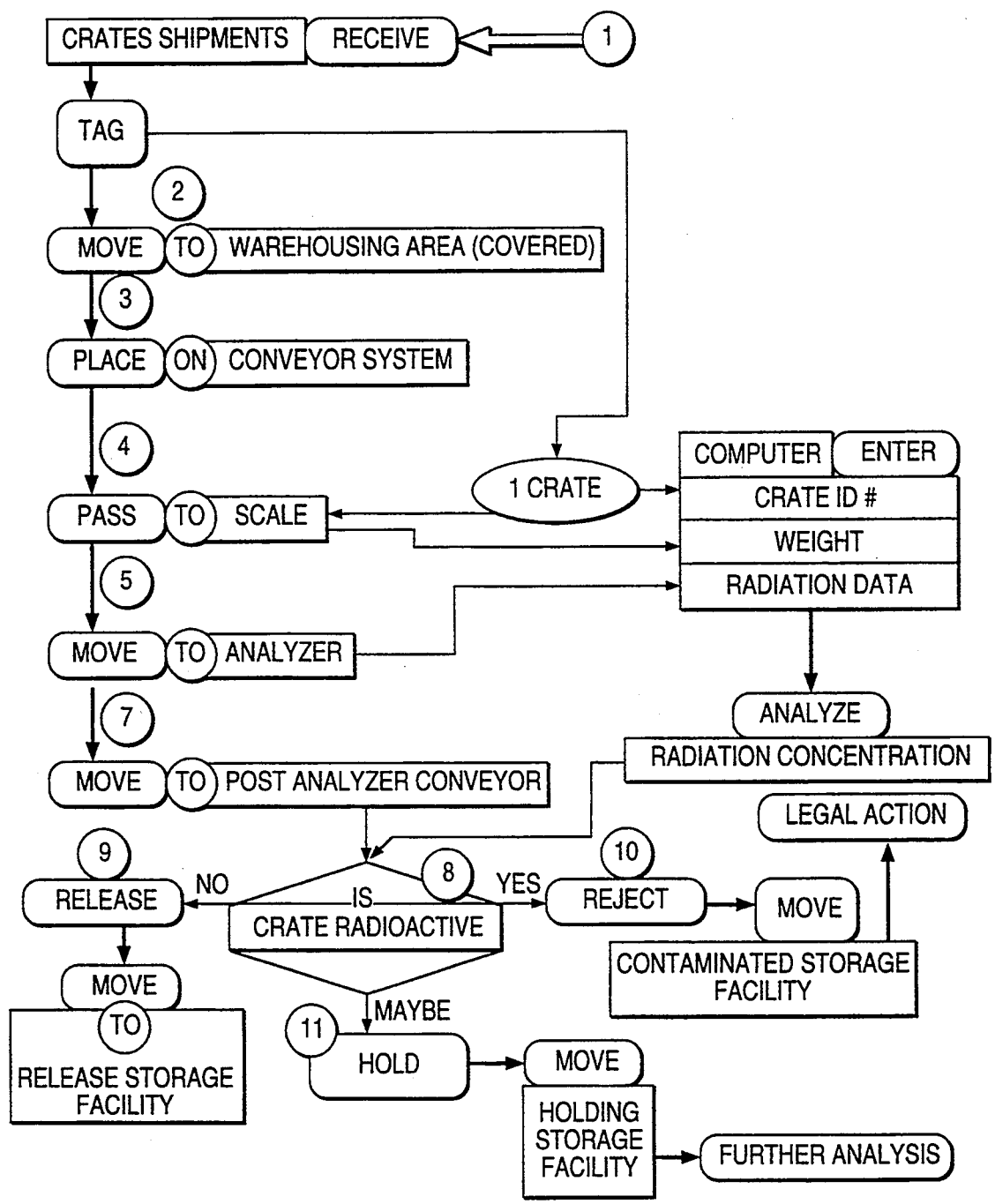
FIG. 29 is a process chart from the container monitoring system.

FIG. 29 is a processor chart similar to FIG. 13, and is used for crates or containers according to the present invention.

An optical bar code scanner such as shown in FIG. 14 can be used for the scanner in the container monitoring system according to the present invention.

Additionally, the data processing logic for the container monitoring system can be that as shown in FIG. 15, except that the block 171 of FIG. 15 showing animal data would be replaced with an equivalent block for crate or container data.

The energy calibration spectrum and frequency calibration of the detectors are substantially identical to that shown in FIG. 16 and 17, for the crate or container monitoring system. Similarly, the tagging system and bar code use of the container monitoring system would be as shown and discussed in FIG. 18. The alternative tagging system and bar code use for the container monitoring system can be that as shown in FIG. 19 discussed hereinabove.

Figure 30:
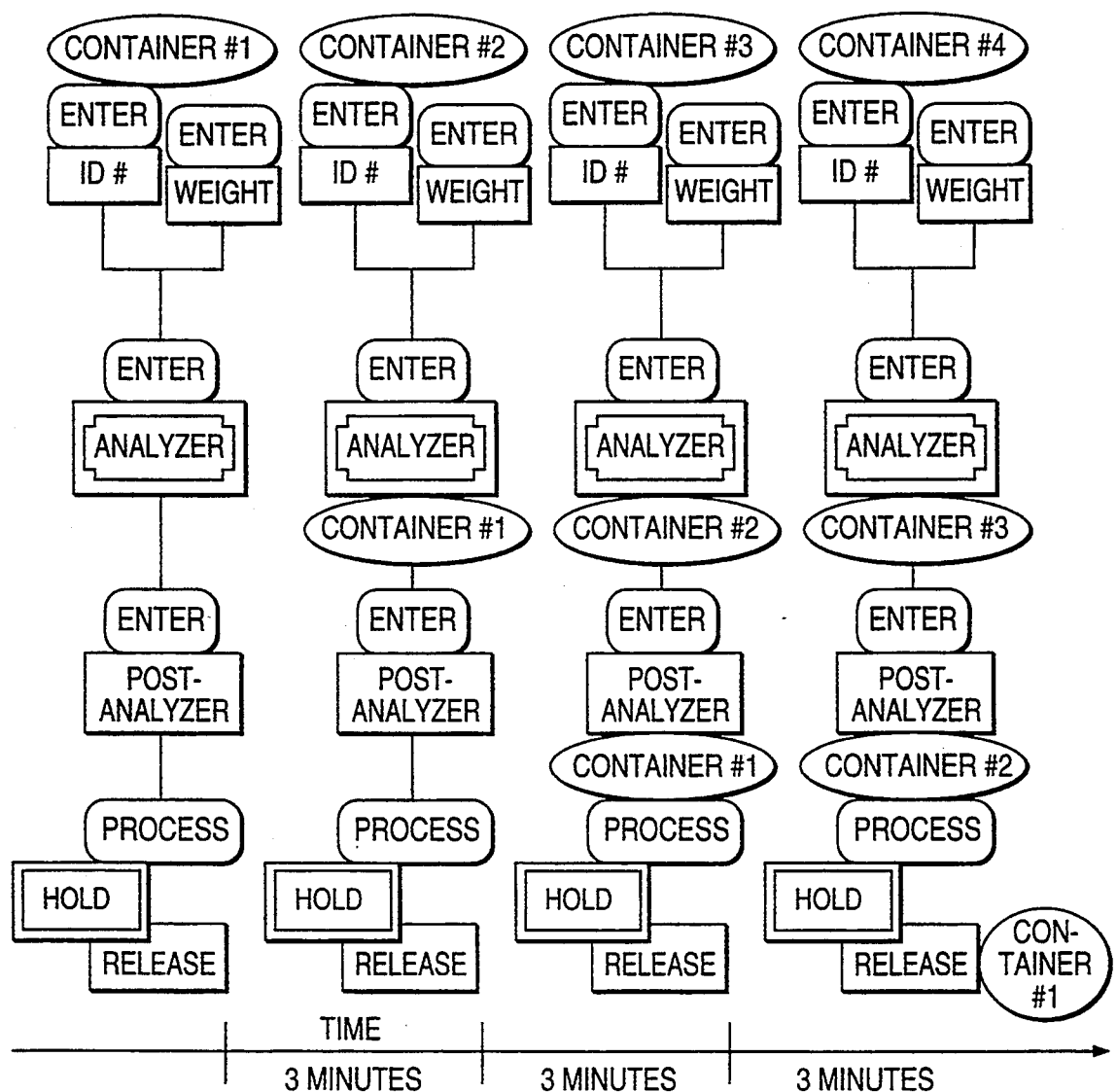
FIG. 30 schematically shows container flow in the container monitoring system.

FIG. 30 illustrates container flow in the container monitoring system of the present invention. Here, containers 1-4 are followed through the process shown in FIG. 30.

Figure 31:
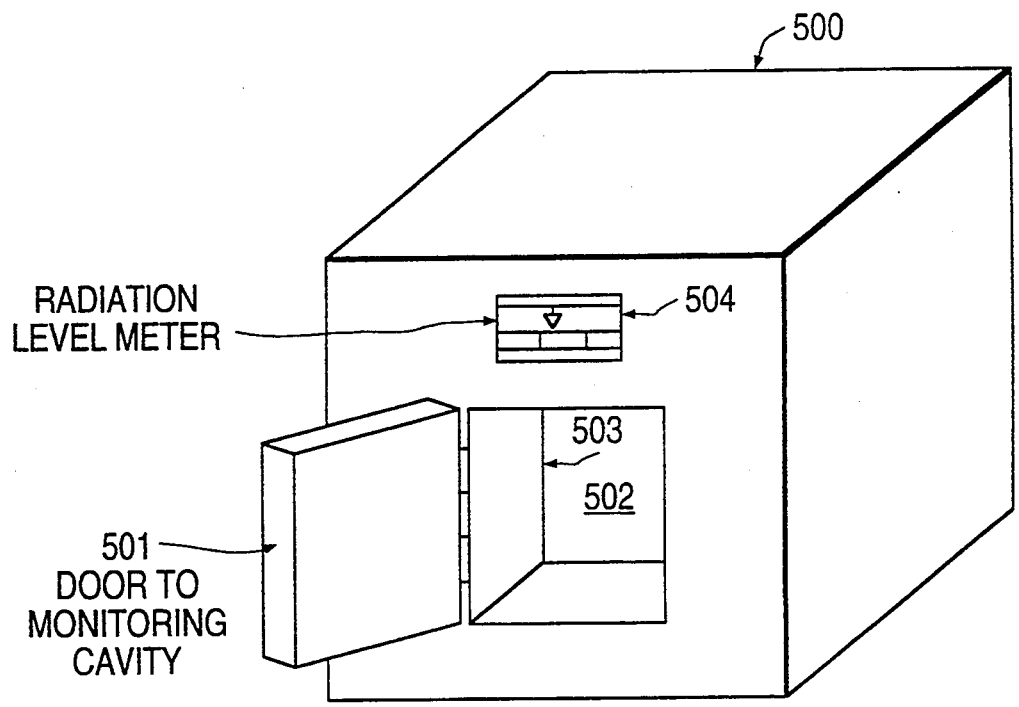
FIG. 31 schematically shows a view of an individual four-detector counter for radiation monitoring of small quantities of foodstuff, beverages, and tobacco.
Figure 32:
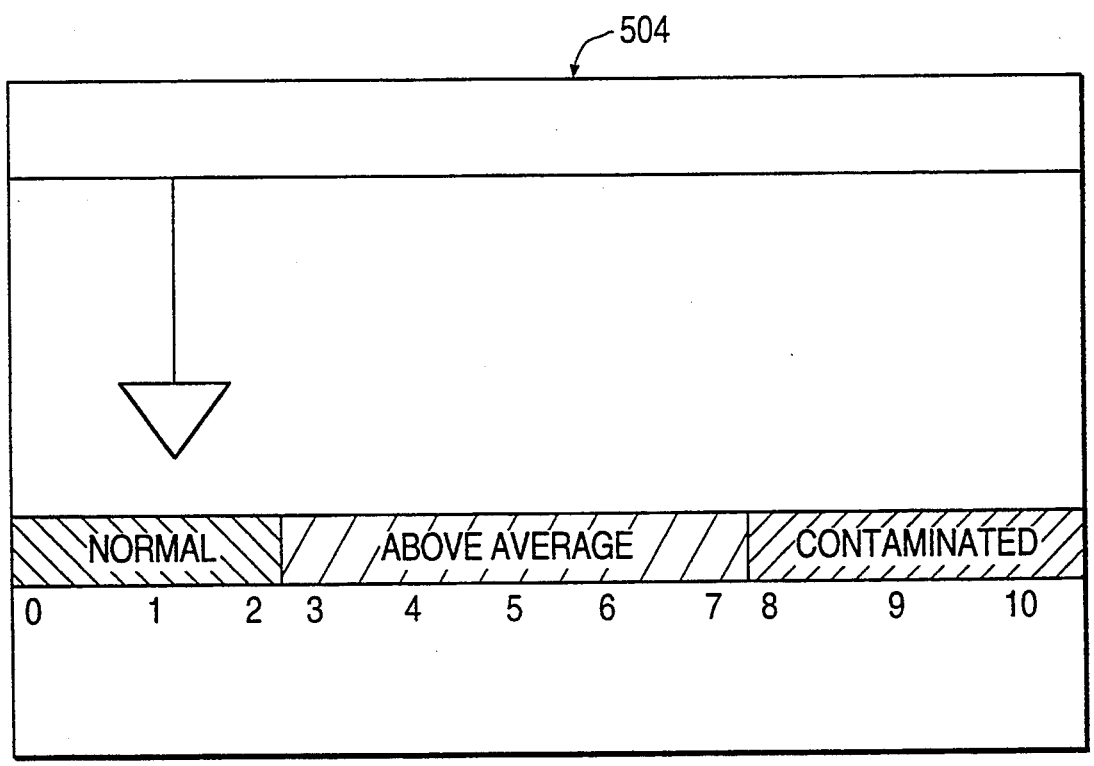
FIG. 32 is a magnified front view of the radiation level meter according to the present invention.

The schematic view shown in FIG. 31 illustrates the four-detector counter equipment for use in radiation monitoring of small quantities of food, beverages or tobacco. The equipment is basically a cubical lead box 500 with a structure similar to a microwave oven. In a preferable embodiment of the present invention the box has dimensions of 36"×36"×36" with 2" thick walls for radiation shielding that weighs about 6,000 pounds, and a 20"×20"×2" door 501 in center of one side for access to a 20"×20"×20" monitoring cavity 502, with ⅛" walls 503 stainless steel or other low radiation-background, durable material to define the area for placing food to be monitored. At the front side, a radiation level meter 504 is used to indicate whether the monitored item is normal, above average, or contaminated based on calibration of the detectors according to allowed food intake or use as shown in the magnified cutaway of the meter 504 in FIG. 32.

Figure 33:
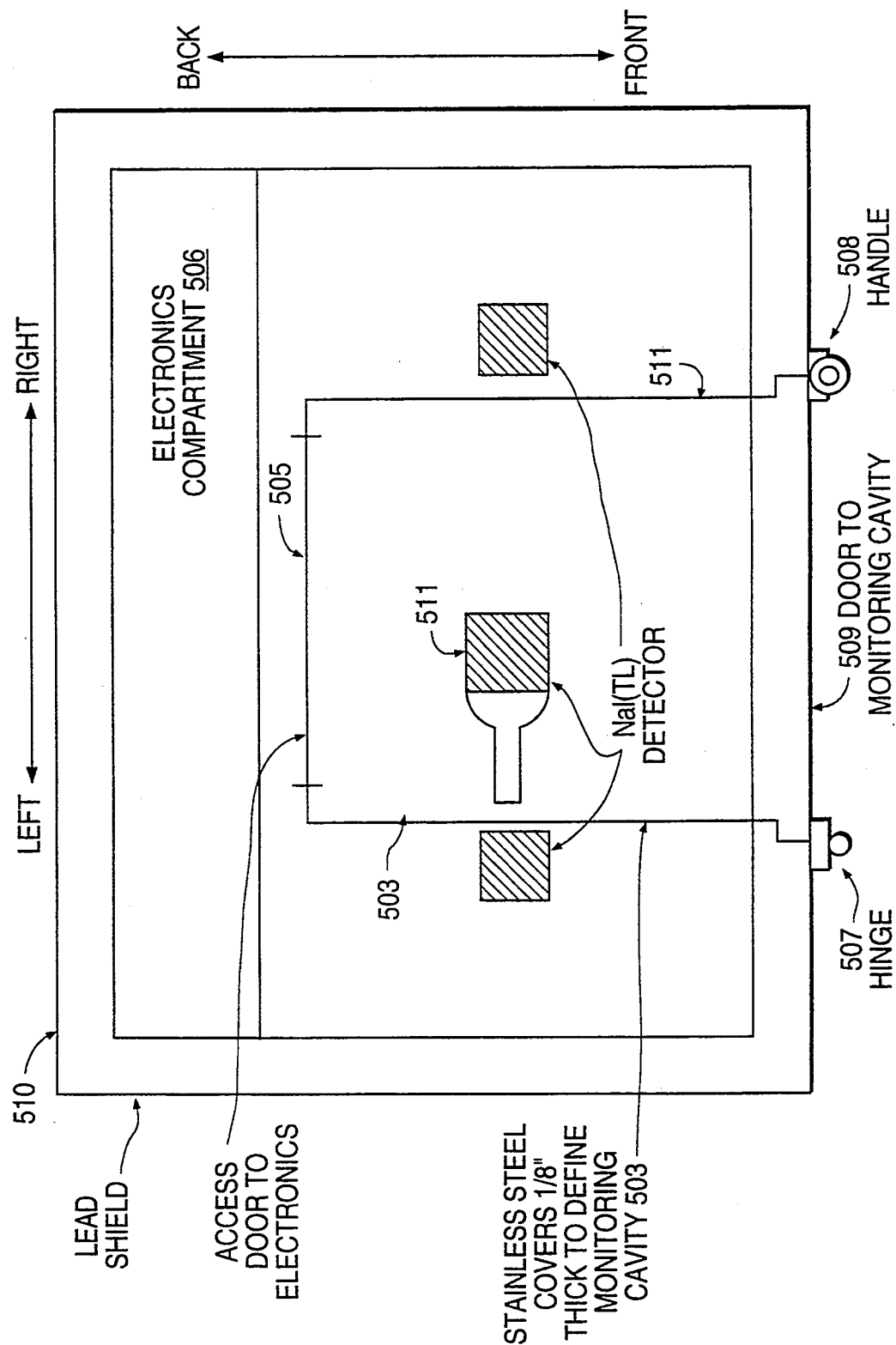
FIG. 33 is a cutaway view down of the system shown in FIG. 31.

FIG. 33 is a cutaway view down of the four-detector counter equipment, showing stainless steel covers 503, with access door 505 to the electronics compartment 506, with a hinge 507 and a handle 508 to operate a rear door 509 to the monitoring cavity, and a lead shield 510. Placed over the cover and on the sides of the cavity are four 4"×4"×4" scintillation NaI (Tl) detectors 511. The electronics include a high voltage bias supply, a single channel analyzer with lower level discriminator and upper level discriminator, a count rate meter and an amplifier.

Figure 34:
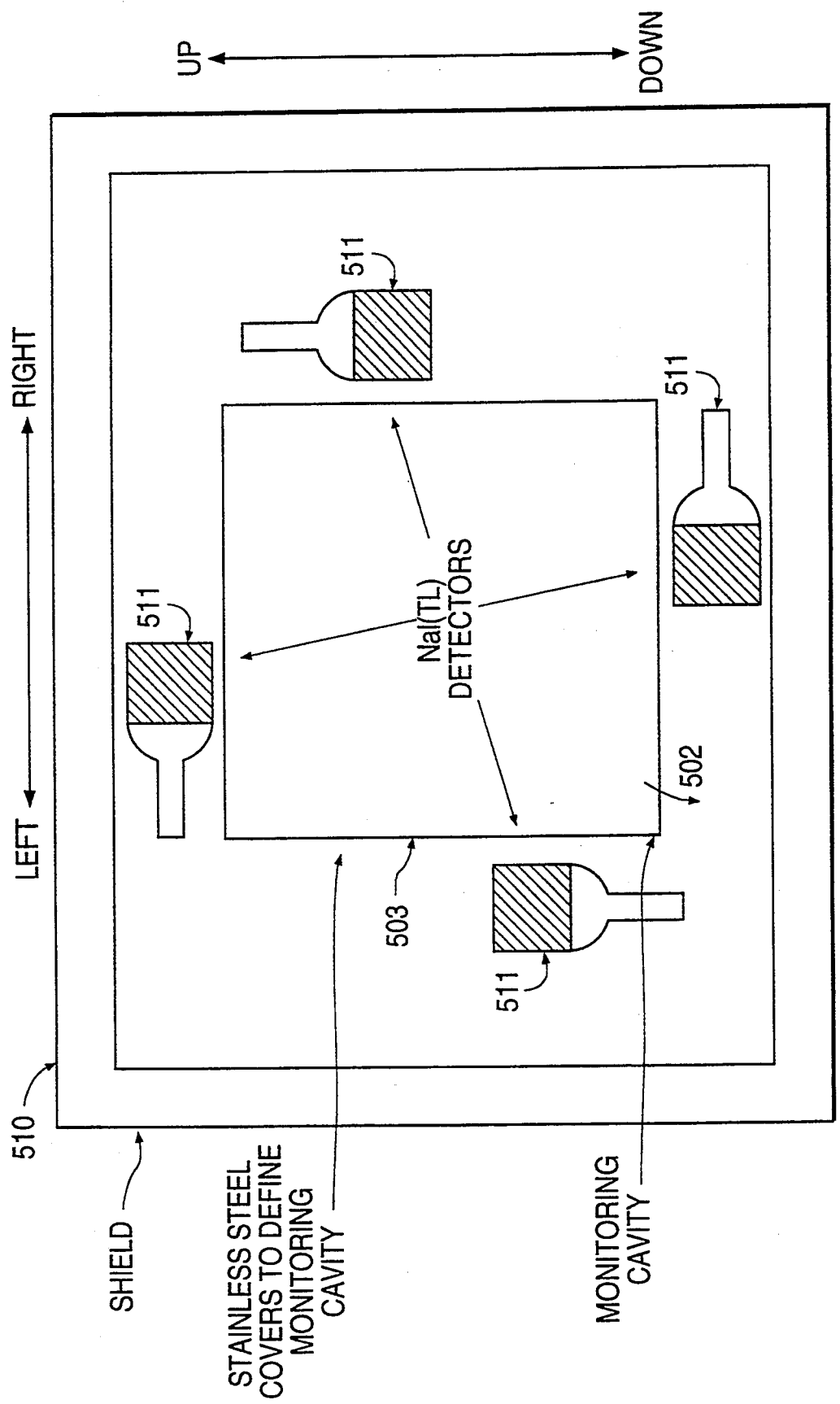
FIG. 34 is a cutaway front looking back of the system shown in FIG. 31.

FIG. 34 is a cutaway front looking back showing the location of the detectors with respect to the monitoring cavity and the shield.

Figure 35:
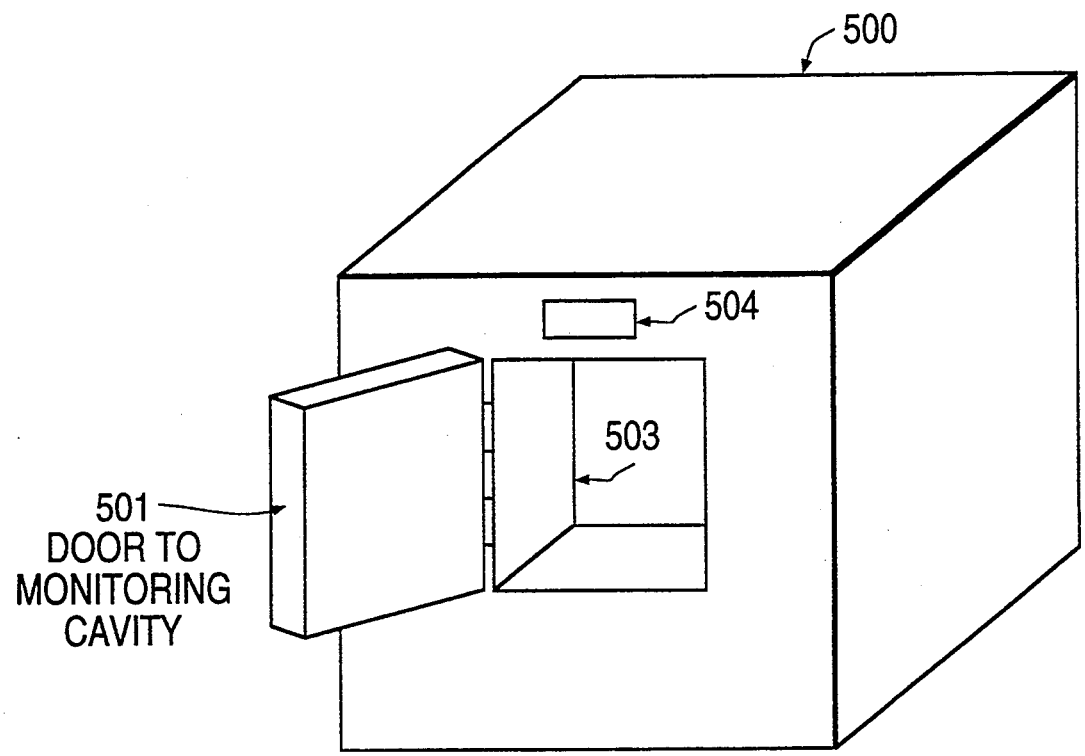
FIG. 35 is a schematic view of a single-detector counter for individual use for radiation monitoring of foodstuff, beverages and tobacco.

FIG. 35 shows the equipment for a one-detector counter system as a lower-cost implementation of the third aspect of the invention for use in radiation monitoring of small quantities of food, beverage, or tobacco. The radiation shield 510, weighs about 3,000 pounds. The lead box 510 measures 24"×24"×30" and the rest of the measurements are similar to the system shown in FIG. 31.

Figure 36:
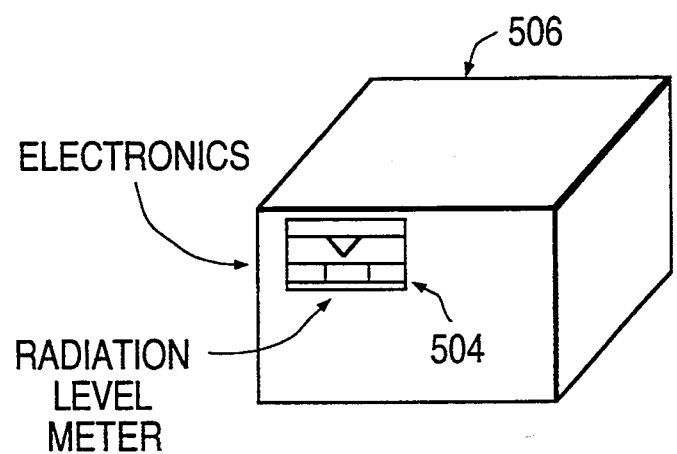
FIG. 36 is a schematic of the electronics compartment and the radiation level meter according to the present invention.

FIG. 36 shows a separate view of the electronics box 506, with the radiation level meter 504.

FIG. 37 is a cutaway view down of the one-detector counter.

FIG. 38 is a cutaway view front to back of the one-detector counter, with a false bottom access to the detector 512.

The individual radiation counter is designed for use by laymen to give gross indication of fitness of food, drinks, or tobacco for individual consumption based on radiation contamination, especially in case of nuclear accidents, fallout, or personal concern. The system is designed to handle small volumes of food, packaged or not, and other items for personal consumption without the need for laboratory analysis or sampling.

While preferred embodiments have been shown and described, it will be understood that the present invention is not limited thereto but may be otherwise embodied with the scope of the present invention.

We claim:

1. A method of monitoring and analyzing an entire body of living animals for nuclear radiation contamination exceeding a predetermined standard comprising:
   directing the animals in a contained single field for serial evaluation of each animal;
   weighing each of said animals one at a time and deriving a weight for each of said animals;

tagging each of said animals with an information indicia for identification;

confining in seriatim each of said animals to a radiation free analysis chamber;

detecting a radiation level of an entire body of each of said animals with at least one detector;

processing said detected radiation level and said weight for each identified animal and generating a radiation concentration;

comparing said radiation concentration with predetermined radioactive material concentration standards for human intake, and;

segregating each of said animals into acceptable or non-acceptable categories relative to said compared radiation concentrations.

2. The method of claim 1 further comprising calibrating said detector with standard calibration levels of radiation.

3. The method of claim 1, further comprising scanning said identifying indicia for identifying each of said animals as to predetermined information.

4. The method of claim 1 further comprising segregating said animals into an intermediate category for further processing.

5. The method of claim 4 further comprising visually indicating the acceptable, nonacceptable or intermediate category of each animal.

6. The method of claim 4 further comprising recording the acceptable, nonacceptable, or intermediate category of each animal.

7. The method of claim 4 further comprising holding each of said animals in an area relative to said acceptable, nonacceptable, or intermediate category.

8. The method of claim 1, wherein said detecting of the radiation level of each of said animals further comprises:

positioning a plurality of said detectors in said confined analysis chamber; and utilizing said weight information for determining a radiation concentration over the whole body of said animal.

9. The method of claim 8 wherein said step of detecting the radiation levels of each of said animals further comprises shielding said detectors from stray radiation from adjoining detectors.

10. The method of claim 1, wherein said step of confining each of said animals in a radiation free analysis chamber further comprises confining said animals for a predetermined time.

11. The method of claim 10 wherein said predetermined time is 2-3 minutes.

12. The method of claim 1 wherein said steps weighing, confining, detecting, processing, comparing and segregating further comprise processing each of said animals for a predetermined time.

13. The method of claim 11 wherein said predetermined time is 4-5 minutes.

14. The method of claim 12 further comprising remote handling.

15. The method of claim 14 wherein said animals are physically separated from operators.

16. The method of claim 1 wherein said radiation free analysis chamber is shielded from natural radiation.

17. The method of claim 16 wherein said shielding of the analysis chamber is a low radiation background material.

18. The method of claim 1 wherein said segregating step further comprises holding said animals in segregated areas relative to said compared radiation concentrations.

19. Apparatus for monitoring and analyzing an entire body of living animals for nuclear radiation levels exceeding a predetermined standard of allowable limits of intake for radioactive materials by the general public comprising:

crowding chute means for directing said animals in serial evaluation of radiation levels for each animal;

a bar coding means to assign identifying indicia for each animal;

a radiation shielded analysis chamber;

a means for directing each of said animals to said radiation shielded analysis chamber;

a processor;

a detector means for detecting the radiation level of an entire body of each of the animals in said radiation chamber; a weighing means for determining a weight of each respective animal; output means for supplying data indicative of said weight and said detected radiation levels of said animal to said processor;

said processor being operative for evaluating and computing said detected information representative of said weight and radiation levels for each of the entire body of said animals and generating an output signal indicative of a radiation concentration value;

a source of standard radiation concentrations, and means for apply said standard radiation concentrations for comparison with the radiation concentration values detected from each animal;

a holding area for animals below a pre-set concentration of radiation and a holding area for animals above a pre-set concentration of radiation; and a means for directing said animals to said holding areas in response to said output signal from said processor indicative of the concentration of detected radiation.

20. Apparatus as set forth in claim 19, wherein said detecting means further comprises a plurality of detector means spectrally positioned in said radiation analysis chamber.

21. Apparatus as set forth in claim 20, wherein said plurality of radiation detector means further comprises positioning a number of detector means in an equal number on both sides of said radiation shielded analysis chamber.

22. Apparatus as set forth in claim 21, further comprising shielding means positioned adjacent each of said radiation detectors.

23. Apparatus as set forth in claim 19, further comprising calibration means for calibrating said detector means.

24. Apparatus as set forth in claim 19, further comprising a scanner for scanning said identifying indicia and for applying the information therefrom to said processor.

25. Apparatus as set forth in claim 19, further comprising first and second gate means and first and second relay means for actuating said first and second gate means respectively, wherein said processor output signal actuates one of said first and second relay means to open one of said first and second gate means.

26. Apparatus as set forth in claim 25, further comprising automation means for actuating said first and second gate means and said first and second relay means.

27. Apparatus as set forth in claim 25 further comprising a third gate means and a third relay means for actuating said third gate means and wherein said processor output signal actuates said third relay means when the radiation concentration of said animal is intermediate an acceptable and nonacceptable limit; and a third holding area for receiving said last named animals when said third gate is actuated.

28. The apparatus of claim 27, further comprising a visual indicating means visually identifying the radiation level of each of the animals relative to said predetermined standard.

29. The apparatus of claim 28, wherein said visual indicating means further comprises red, amber, and green lights.

30. The apparatus of claim 27, further comprising recorder means for recording the output signal from said processor.

31. The apparatus of claim 27, wherein said radiation shielded analysis chamber comprises an enclosed area comprised of heavy gauge steel.

32. The apparatus of claim 31, wherein the interior of said enclosed area is sealed with stainless steel.

33. The apparatus of claim 31, wherein said heavy gauge steel is thick enough to shield against natural radiation.

34. The apparatus of claim 31, wherein said detector means further comprises means for fixedly positioning said detector means within said enclosed area.

35. Apparatus for monitoring and analyzing whole containers and their contents for nuclear radiation levels exceeding predetermined radiation standards, comprising:
   directing means for directing said containers in serial evaluation of radiation levels for each container;
   a scale means for weighing each of said containers;
   a radiation shielded analysis chamber; and,
   a means for directing each of said containers to said radiation analysis chamber;
   a detector means for detecting the radiation level of contents of each of the containers in said radiation chamber, and means for supplying said weight information and said detected radiation levels to a processor;
   said processor being operative for evaluating and computing said detected information representative of weight and radiation levels for each of said containers and generating an output signal indicative of a radiation concentration value of the contents;
   a source of standard radiation concentrations, and means for applying said standard radiation concentrations for comparison with the radiation concentrations detected from each container;
   a holding area for containers below a pre-set concentration of radiation and a holding area for containers above a pre-set concentration of radiation;
   a means for directing said containers to said holding areas in dependence on said concentration of detected radiation.

36. Apparatus as set forth in claim 35, wherein said detecting means further comprises a plurality of detector means positioned in said radiation analysis chamber.

37. Apparatus as set forth in claim 36, wherein said plurality of radiation detector means further comprises positioning a number of detector means in an equal number on both sides of said radiation shielded analysis chamber.

38. Apparatus as set forth in claim 37, further comprising shielding means positioned adjacent each of said radiation detectors.

39. The apparatus of claim 38, wherein said radiation shielded analysis chamber comprises an enclosed area comprised of heavy gauge steel.

40. The apparatus of claim 39, wherein the interior of said enclosed area is sealed with stainless-steel.

41. Apparatus as set forth in claim 35, further comprising calibration means for calibrating said detector means.

42. Apparatus as set forth in claim 35, further comprising first and second gate means and first and second relay means for actuating said first and second gate means respectively wherein said processor actuates one of said first and second relay means to open one of first and second said gate means.

43. Apparatus as set forth in claim 42 further comprising a third gate means and a third relay means for actuating said third gate means and wherein said processor actuates said third relay means when the radiation concentration of said container is intermediate an acceptable and nonacceptable limit; and a third holding area for receiving said last named containers when said third gate is actuated.

44. The apparatus of claim 43, further comprising a visual indicating means visually identifying the radiation level of each of the containers relative to said predetermined standard.

45. The apparatus of claim 44, wherein said visual indicating means further comprises red, amber, and green lights.

46. The apparatus of claim 43, further comprising recorder means for recording the output signal from said processor.

47. The apparatus of claim 35, wherein said heavy gauge steel is thick enough to shield against natural radiation.

48. Apparatus for monitoring small quantities of foodstuff, beverages, and tobacco for nuclear radiation levels exceeding a predetermined standard for allowable human intake, comprising:
   a radiation monitoring cavity means with low radiation background, durable wall to define the monitoring cavity and the area for placing goods to be monitored;
   a radiation shielding means forming the exterior walls of the monitoring cavity;
   a housing means for housing the monitoring cavity and the components of the apparatus;
   an access means in the center of one side of the housing to access the monitoring cavity;
   a radiation count rate means for measuring the radiation level of each of the quantities of goods in said monitoring cavity;
   a radiation analysis means with lower and upper level discriminators;
   said radiation count rate means to indicate normal and contaminated levels in said radiation monitoring cavity;
   an electronics means to supply high voltage to said radiation count rate means and amplify count rate signals provided by said radiation count rate means;
   an access means to the said radiation count rate means; and
   an access means to the said electronics means.

49. Apparatus as set forth in claim 48, wherein said detecting means further comprises a plurality of detector means positioned in said radiation monitoring cavity.

50. Apparatus as set forth in claim 49, wherein said plurality of radiation detector means further comprises a plurality of detector means in an equal number on each side of said radiation monitoring cavity means.

51. Apparatus as set forth in claim 48, wherein said detecting means further comprises a single detector means positioned at the bottom of said radiation monitoring cavity.

52. Apparatus as set forth in claim 48, further comprising calibration means for calibrating said detector means.

53. The apparatus of claim 52, wherein calibration means are based on standard annual limits of intake of radioactive materials.

54. The apparatus of claim 48, further comprising a visual indicating means visually identifying the radiation level of each monitored item relative to said predetermined standards for human intake.

55. The apparatus of claim 54, wherein said visual indicating means further comprise red, amber, and green lights.

56. The apparatus of claim 55, wherein said visual indicating means further comprises numerical values from zero to ten corresponding to the radiation level in said monitoring cavity, with ten as the highest level.

57. The apparatus of claim 48, wherein said radiation shielding means comprises an enclosed area comprised of thick lead wall.

58. The apparatus of claim 57, wherein said enclosed area is lined with stainless steel.

59. The apparatus of claim 58, wherein said enclosed area defines said radiation monitoring cavity.

60. A method for monitoring and analyzing small quantifies of various goods for nuclear radiation levels exceeding a predetermined standard for human use comprising:

confining the goods to be monitored in a contained radiation free monitoring chamber;

detecting the radiation level of a quantity of said goods to be monitored, recording said detected radiation level, and;

comparing detected radiation levels with predetermined radiation standards.

61. The method of claim 60, wherein said step of confining each of said goods in a radiation free monitoring chamber further comprises confining said goods for a predetermined time.

62. The method of claim 61, wherein said predetermined time is 3–4 minutes.

* * * * *